United States Patent
Tribble et al.

(10) Patent No.: US 12,001,438 B2
(45) Date of Patent: *Jun. 4, 2024

(54) CONTROLLED SUBSTANCE DIVERSION DETECTION SYSTEMS AND METHODS

(71) Applicant: CareFusion 303, Inc., San Diego, CA (US)

(72) Inventors: Dennis Anthony Tribble, Ormond Beach, FL (US); Scott Loebig, Encinitas, CA (US); Thomas William Utech, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 107 days.

This patent is subject to a terminal disclaimer.

(21) Appl. No.: 17/151,040

(22) Filed: Jan. 15, 2021

(65) Prior Publication Data

US 2021/0133201 A1 May 6, 2021

Related U.S. Application Data

(63) Continuation of application No. 15/294,628, filed on Oct. 14, 2016, now Pat. No. 10,915,604.

(Continued)

(51) Int. Cl.
*G16H 20/13* (2018.01)
*G06F 16/2457* (2019.01)
(Continued)

(52) U.S. Cl.
CPC .... *G06F 16/24578* (2019.01); *G06F 16/9535* (2019.01); *G16H 20/13* (2018.01); *G16H 40/20* (2018.01); *G16H 70/40* (2018.01)

(58) Field of Classification Search
CPC .......... G06F 16/24578; G06F 16/9535; G06F 17/30; G16H 40/20; G16H 70/40;
(Continued)

(56) References Cited

U.S. PATENT DOCUMENTS

| 6,842,736 B1 | 1/2005 | Brzozowski |
| 8,606,596 B1 * | 12/2013 | Bochenko .............. G06Q 10/00 705/2 |

(Continued)

FOREIGN PATENT DOCUMENTS

| CN | 102648481 A | 8/2012 |
| CN | 104828317 A | 8/2015 |
| WO | WO-2014127234 A1 | 8/2014 |

OTHER PUBLICATIONS

European Office Action for Application No. 16787681.2, dated Nov. 6, 2019, 9 pages.

(Continued)

*Primary Examiner* — Alaaeldin M Elshaer
(74) *Attorney, Agent, or Firm* — Morgan, Lewis & Bockius LLP

(57) ABSTRACT

Systems and methods are provided for identifying and tracking diverters of controlled medications. A system may receive signals indicative of medication dispensing activities by one or more health care providers such as nurses, physicians, or pharmacists. Based on the received signals, the system may determine suspected diverters and provide a graphical interface identifying corresponding factors related to usage, waste, dosage, or other factors associated with the suspected diverters. The graphical interface may provide a list of top diverters and display dispensing transactions performed at a dispensing device.

16 Claims, 26 Drawing Sheets

Related U.S. Application Data

(60) Provisional application No. 62/242,583, filed on Oct. 16, 2015.

(51) Int. Cl.
  *G06F 16/9535* (2019.01)
  *G16H 40/20* (2018.01)
  *G16H 70/40* (2018.01)

(58) Field of Classification Search
  CPC ........ G16H 20/13; G16H 10/60; G16H 15/00; G07F 11/00; G06Q 50/00; G06Q 10/00; A61J 7/00
  USPC .......................................................... 705/2, 3
  See application file for complete search history.

(56) References Cited

U.S. PATENT DOCUMENTS

| | | | |
|---|---|---|---|
| 8,768,724 B2 | 7/2014 | Miller | |
| 9,636,273 B1 | 5/2017 | Sprintz | |
| 2003/0229519 A1 | 12/2003 | Vahlberg | |
| 2007/0100216 A1 | 5/2007 | D'Amato | |
| 2008/0059226 A1* | 3/2008 | Melker | G16H 40/67 705/2 |
| 2008/0190953 A1* | 8/2008 | Mallett | B07C 7/005 221/13 |
| 2011/0161108 A1* | 6/2011 | Miller | G06Q 30/0185 705/3 |
| 2013/0018921 A1* | 1/2013 | Jin | G06F 21/6245 707/E17.001 |
| 2014/0114962 A1* | 4/2014 | Rosenburg | G06F 16/2423 707/723 |
| 2014/0297306 A1* | 10/2014 | Whiddon | G16Z 99/00 705/2 |
| 2015/0339456 A1* | 11/2015 | Sprintz | G16H 50/30 705/3 |
| 2017/0083681 A1 | 3/2017 | Radcliffe | |
| 2017/0109480 A1* | 4/2017 | Vahlberg | A61J 7/0084 |
| 2018/0247703 A1 | 8/2018 | Harris | |

OTHER PUBLICATIONS

International Preliminary Report on Patentability of Application No. PCT/US2016/057158, dated Jan. 4, 2018, 19 pages.
International Search Report and Written Opinion for Application No. PCT/US2016/057158, dated Dec. 22, 2016, 10 pages.
Australian Office Action for Application No. 2016338693, dated Dec. 1, 2021, 4 pages.
Chinese Office Action for Application No. 201610903488.8, dated Nov. 11, 2021, 4 pages including translation.
Australian Office Action for Application No. 2016338693, dated Mar. 18, 2021, 5 pages.
Chinese Office Action for Application No. 201610903488.8, dated Apr. 2, 2021, 22 pages including translation.
Canadian Office Action for Application No. 3001135, dated Dec. 2, 2022, 4 pages.
Extended European Search Report for Application No. 22200495.4, dated Jan. 20, 2023, 12 pages.

* cited by examiner

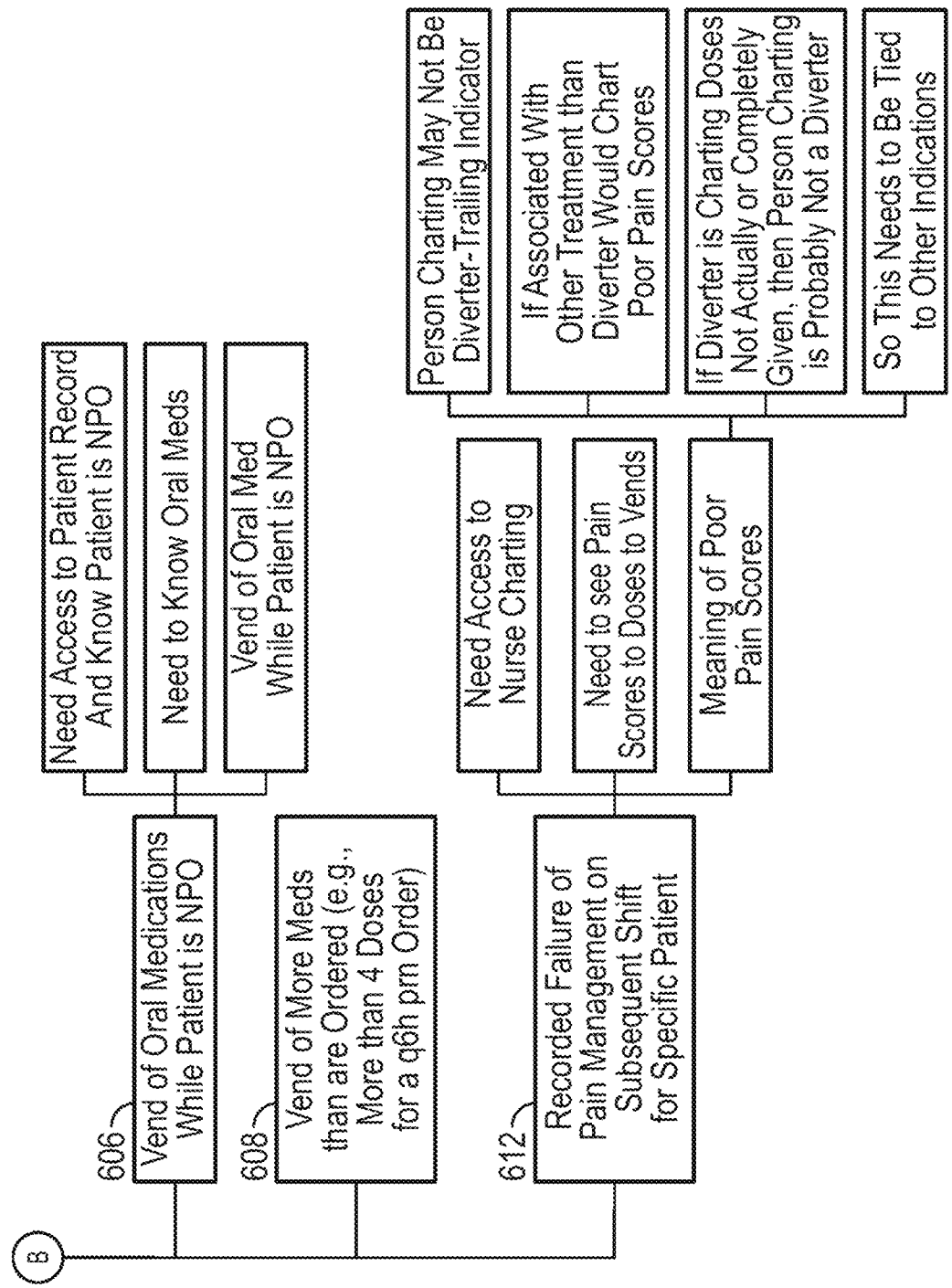

Advanced Diversion Scoring

| # | Configuration | Scoring Criteria | Strong/Weak Indicator |
|---|---|---|---|
| 1 | Total Score — All (302) — 800 | 1) Sum scores for waste, usage, dose, hardware, scheduling, and discrepancy scores for each provider<br>2) Report the top *n* providers in descending order by score where *n* is configurable at a site level. | |
| 2 | Waste (801) — Total Waste Score (400) — 804 | 1) Perform the following strong indicator analyses<br>2) Sum the strong scores from each analysis<br>3) Identify users with strong scores (strong score > ???)<br>4) Perform weak analyses on users who have strong scores<br>5) Sum the scores by provider into a gross waste score for that provider | Strong (802) |
| 3 | More Waste than normal (402) — 806 | 1) Locate all transactions involving waste by care area.<br>2) Compute a mean occurrence number and a standard deviation of that mean for each care area<br>3) Identify any users whose waste occurrence is more than 2 standard deviations of the mean.<br>4) Score based on deviation<br>   a. 1 = 2 – 2.5 SD<br>   b. 2 = 2.6 – 3 SD<br>   c. 3 = 3.1 – 4 SD<br>   d. 4 = > 4 SD | Strong (802) |

FIG. 8

| Calculation ID | Care Criteria | Instructions | Strength of the Indicator |
|---|---|---|---|
| 13 | Usage | Escalating Usage over reporting period for care area 1400 | 1) Using the query for care area, assess weekly usage from the beginning to the end of the report period.<br>2) If starting weekly usage > 0, report each subsequent week as a multiple of the mean usage<br>   a. If the weekly usage for the last week > mean + 1 SD of average, score = SD above mean.<br>3) If starting weekly usage = 0, user was probably away on PTO and escalation would be normal. | Strong ← 802 |
| 14 | | Distributed ADC usage 310 | 1) Summarize all controlled substance vends for each patient by ADC in a care area.<br>2) Compute a primary ADC for each patient as the ADC with the largest number of vends for that patient for the reporting period.<br>3) Summarize all controlled substances vends for the care area by patient by caregiver by ADC.<br>4) Report proportion of vends at non-primary ADC for each patient for each caregiver sorted in descending order by proportion of non-primary vends.<br>5) Compute a mean number of non-primary vends per patient.<br>6) Report top 5 users whose non-primary vends for any patient exceeds the mean of non-primary vends for that patient by more than 1 SD of mean. Sort in descending order by #SD of non-primary vends.<br>7) Score = #SD above mean | Strong ← 802 |

1402 (points to row 13 instructions)
1404 (points to row 14 instructions)

FIG. 14

| Indicator Number | Indicator Category | Scenario Name | Scenario Description | Strength of Indicator (Initially) |
|---|---|---|---|---|
| 15 | Usage | Vend for a discharged patient ↙ 312 | 1500 { 1) Should never occur; discharged patients remain active primarily to permit resolution of waste or discrepancy counts.<br>2) NOTE: reported incident involved a nurse stealing to sell on the street and both the vend on discharged patient, and the volume taken were unusual.<br>3) Score is number of vends over reporting period. Vast majority of people should have 0. | Strong ← 802 |
| 16 | | Vend at an ADC which does not normally serve that patient ↙ 314 | 1502 { 1) For each patient served by a suspect indicated by strong indicators, identify each vend where the ADC used was used only by the suspect for serving that patient.<br>2) Score = number of vends at abnormal ADC.<br>3) Sort in descending order by abnormal vend score and report top five abnormal vends.<br>4) ?? Exclude vends from procedural areas?? | Weak ← 802 |
| 17 | | Removal of outdates ↙ 1516 | 1504 { 1) For each care area, list the removal of outdated controlled substance products from each med station by user.<br>2) Compute a mean removal number per user.<br>3) Compute the standard deviation of that mean.<br>4) Compute deviation from the mean as a number of standard deviations of the mean.<br>5) Report any users whose removal of controlled substances is more than 1 SD above the mean; score is the number of SD's above the mean. | |

FIG. 15

| | Outcome Measure | Evaluation/ Calculation | Strength of Indicator |
|---|---|---|---|
| 18 | Dose Score — 600 ← 1601 | Dose Score — 600 1) Requires vend and administration data. 2) Expectation is that vend data results in administration data 3) Expectation is that vended dose should be the same as administered dose 4) Expectation is that product vended for a dose should be the same across providers 5) Expectation is that patient's dose requirement should be nearly the same across providers. A provider who always gives more (or dramatically less) than what the patient ordinarily gets is suspect  ⟵ 1600 | |
| 19 | Dose | No administration for vend ← 1602  1) For each patient in a care area, match up each vend with an administration 2) Report all vends for which no dose was given grouped by caregiver (Note: there should be none) 3) Sort resulting caregivers by number of vends without dose record descending. 4) Report top five caregivers; score = number of no-dose vends.  ⟵ 1604 | Strong ← 802 |

FIG. 16

| | Case Checklists | Case Questioning | Priority Indicators | Suggested Indicator Strength |
|---|---|---|---|---|
| 22. | Dose | Doses higher than other caregivers by frequency ← 614 | patient, compute the score as the number of SD above the mean for all users.<br>1) For each patient cared for by a suspect based on strong indicators, determine the average number of doses per shift the patient received from all caregivers.<br>2) Determine the standard deviation of the mean for that average.<br>3) For each patient cared for by a suspect based on strong indicators, determine the average dose given to the patient at each administration.<br>4) Compute the standard deviation of that mean.<br>5) For each suspect user who cared for that patient, determine the average number of doses per shift administered by that caregiver.<br>6) If the number of doses per shift is less than or equal to mean + 1 SD from the mean, set the score = 0 (not applicable to this criterion)<br>7) Compute the mean dose frequency for the suspect and report the score as the number of SD above the mean.  ← 1900 | Weak ← 802 |
| 23. | | Doses patient lower and wastes more ← 619 | 1) Determine mean dose for all caregivers and determine if any caregivers doses the patient more than 1 SD less than the mean of all caregivers.<br>2) Compute the amount of waste per dose and compare to other caregivers. If more than 1 SD higher then score as number of SD's  ← 1902 | Weak ← 802 |

FIG. 19

| # | Dose | Confirmation | Methodology | Strong/Weak |
|---|---|---|---|---|
| 24 | | Withdrawal from multiple NDC's for the same patient ← 602 | 1) Same as number 14 focused only on the patients cared for by a suspect caregiver | Weak ← 802 |
| 25 | | Premature Vend ← 604 (2002) | 1) Needs medication administration data.<br>2) For each suspected caregiver locate transactions where the vend occurs more than an hour before the medication administration is documented in the eMAR.<br>3) Score as the number of doses vended more than 1 hour before administration. | Weak ← 802 |
| 26 | | Vend of oral med for NPO patient ← 606 (2004) | 1) Acquire list of patients who were NPO during medication administration (needs interface)<br>2) Search all vends for those patients for oral medications<br>3) Score is the number of vends. | Strong ← 802 |
| 27 | | Vend of more doses than permitted in the order ← 608 (2006) | 1) For each patient cared for by a suspect patient, review their orders and determine the maximum number of permitted doses per shift per each order.<br>2) Count the number of vends per shift by each caregiver and determine if any had more vends than permitted by the order.<br>3) Score is the number of excess vends. | Weak ← 802 |
| 28 | | Pain medications given without a pain assessment ← 610 (2008) | 1) Requires access to nurse charting<br>2) Would probably need to capture how often this omission happens normally and then look for higher numbers. | Weak ← 802 |
| 29 | | Failure of dose to manage pain ← 612 (2010) | 1) Requires nurse charting information – assessment after administration<br>2) Points backward at caregiver<br>3) Might work if we looked for rate/suspect | Weak ← 802 |

FIG. 20

| Component | Score Computation | Count (Score) | Computation | Creates Alert (Yes/No) |
|---|---|---|---|---|
| 30 | Scheduling | Total 2100 | 1) Sum of individual scheduling scores<br>2) Requires access to scheduling system | Strong |
| 31 | | Vends when not on duty 500 (502) | 1) For each user, determine a table of on-duty hours<br>2) Add a buffer of 1 hour in each direction for documentation<br>3) Search the vend data for vends that occurred outside scheduled hours.<br>4) How to handle double-shifts/overtime?<br>5) Score is number of off-shift vends | ↓ 802 |
| 32 | | Vends on evenings and nights 504 (2104) | 1) Search suspects for vends on evenings and nights.<br>2) Search users on evenings and nights who may not normally be scheduled on evenings or nights<br>3) Search for users whose vend activity is higher on weekends than during the week | Weak ↓ 802 |
| 33 | | Occasional Staff 508 (2108) | 1) If suspected user is occasional staff, score = 1, else score = 0<br>2) Highlights occasional staff | Weak ↓ 802 |
| 34 | | Weekend vends 506 (2106) | 1) If suspect user works weekends, look for evidence that vend rates are higher on weekends than during the week | Weak ↓ 802 |
| 35 | Discrepancy 2901 | Total 700 (2110) | 1) For each care area, determine the list of users.<br>2) For each user, determine the number of reported discrepancies<br>3) Compute the average number of reported discrepancies<br>4) May be reverse pointing... look at previous users from scheduling data. | Weak ↓ 802 |

FIG. 21

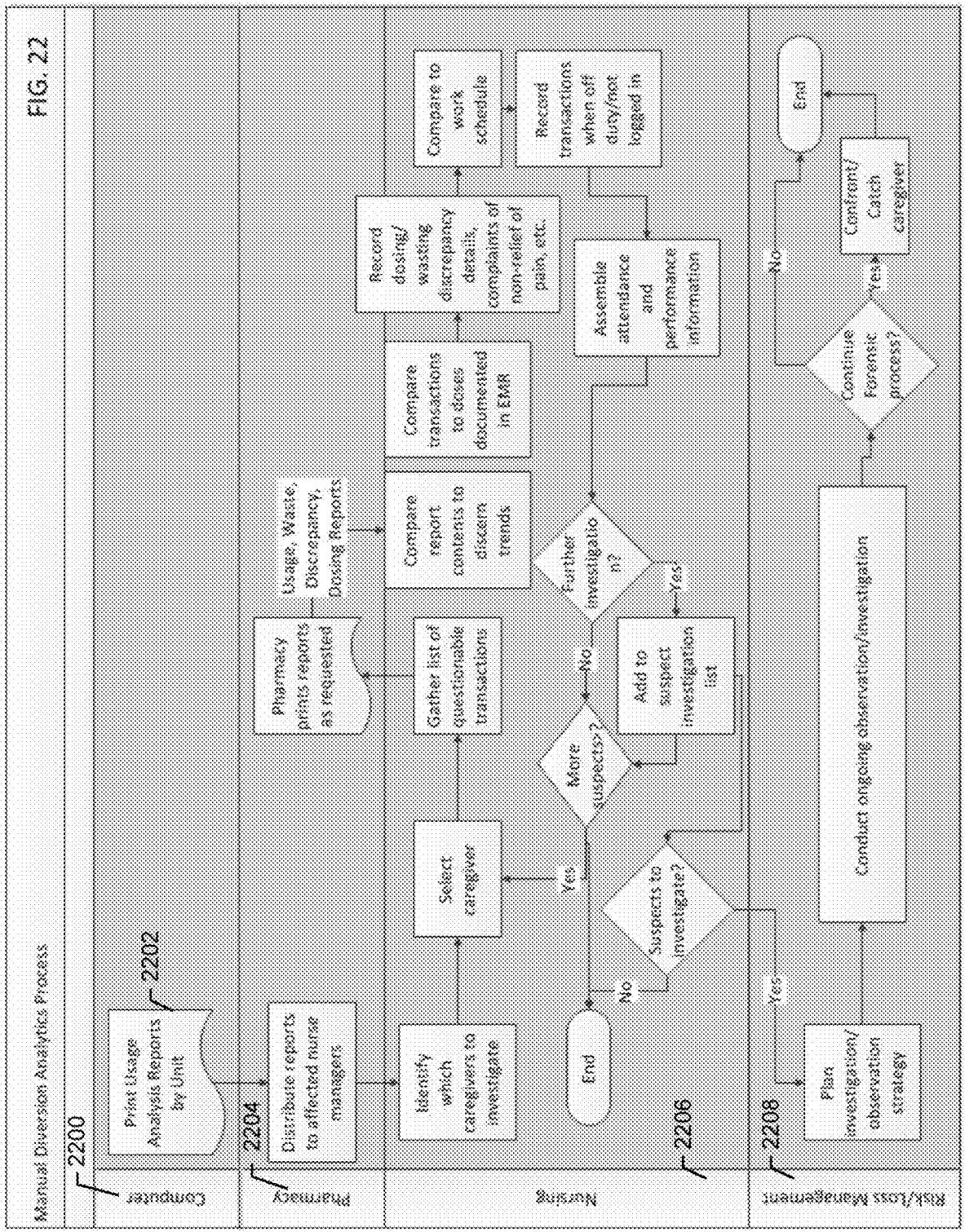

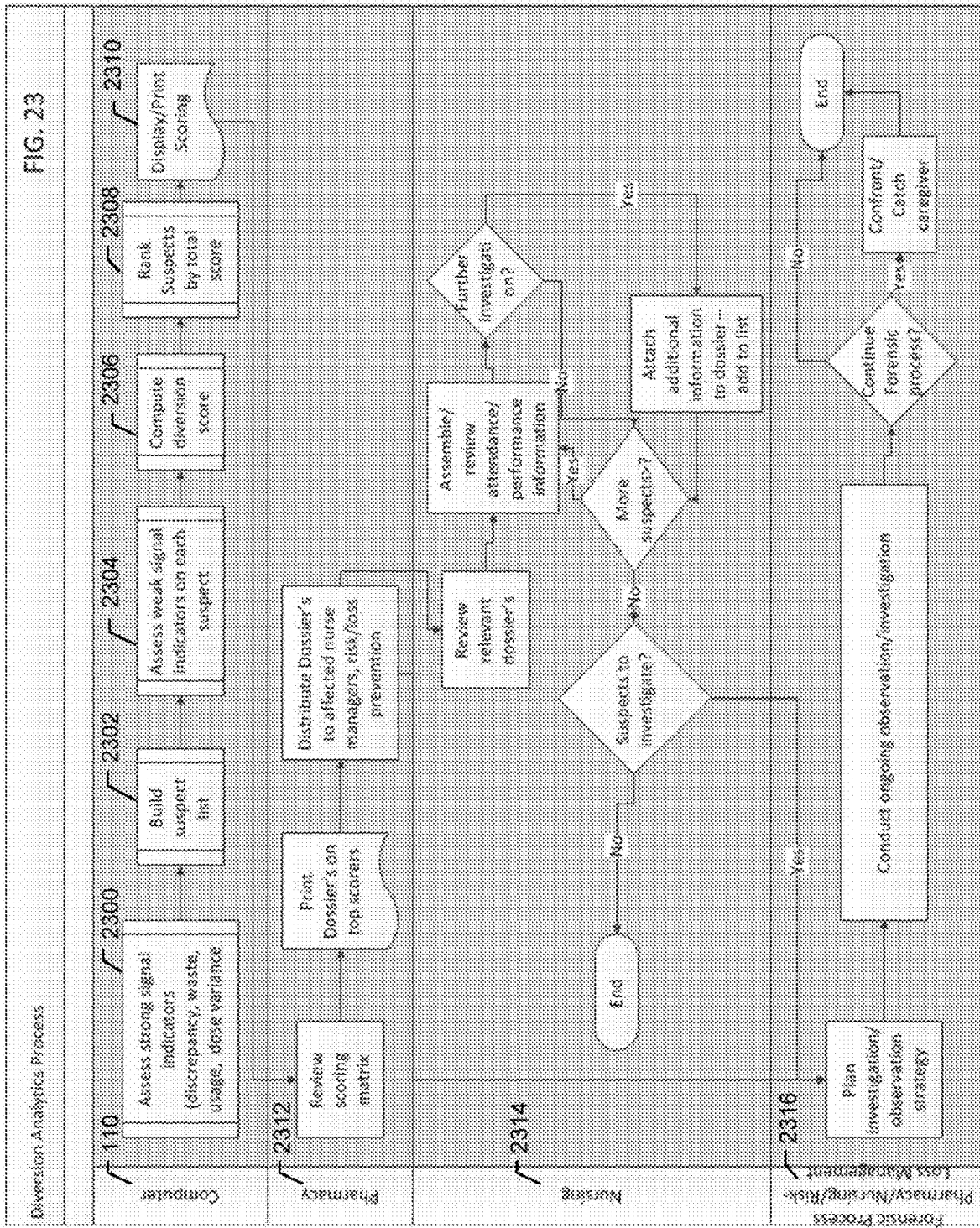

CONTROLLED SUBSTANCE DIVERSION DETECTION SYSTEMS AND METHODS

CROSS-REFERENCE TO RELATED APPLICATIONS

This application is a continuation application of U.S. application Ser. No. 15/294,628, entitled "CONTROLLED SUBSTANCE DIVERSION DETECTION SYSTEMS AND METHODS," filed on Oct. 14, 2016, now U.S. Pat. No. 10,915,604, which claims the benefit of priority from U.S. Provisional Application Ser. No. 62/242,583, entitled "CONTROLLED SUBSTANCE DIVERSION DETECTION SYSTEMS AND METHODS," filed on Oct. 16, 2015, the entirety of each of which is incorporated herein by reference.

BACKGROUND

The present disclosure generally relates to controlled substance diversion, and more particularly to controlled substance diversion detection systems and methods.

SUMMARY

In accordance with various aspects of the present disclosure, a method is provided for identifying a potential controlled medication diverter, the method including: automatically monitoring dispensing of a controlled medication from a medication dispensing device; receiving one or more signals associated with a health care provider who dispensed the controlled medication; determining, by one or more processors, one or more factor scores, wherein each factor score is associated with one or more of the received signals; determining, by one or more processors, a diversion score based on one or more of the determined factor scores; and determining, by one or more processors, if the health care provider is a potential controlled medication diverter based on the diversion score.

In accordance with other aspects, a non-transitory machine-readable medium is provided embodying instructions that, when executed by a machine, cause the machine to perform a method for identifying a potential controlled medication diverter, the method including: automatically date stamping, time stamping, or user stamping, by a medication dispensing device, each dispensing transaction performed at the medication dispensing device; receiving one or more signals associated with a health care provider who dispensed the controlled medication; determining one or more factor scores, wherein each factor score is associated with one or more of the received signals; determining a diversion score based on one or more of the determined factor scores; and determining if the health care provider is a potential controlled medication diverter based on the diversion score.

In accordance with other aspects, a system for identifying potential controlled medication diverters is provided, the system including: one or more automated dispensing cabinets; one or more processors; and a memory including instructions that, when executed by the one or more processors, cause the one or more processors to: automatically monitor dispensing of controlled medications from the one or more automated dispensing cabinets; receive signals associated with each health care provider who dispenses controlled medications from the one or more automated dispensing cabinets; determine a factor score for each of the received signals; determine a diversion score based on one or more of the determined factor scores; and determine which of the health care providers are potential controlled medication diverters based on the determined diversion scores.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIGS. 6A-6C illustrate a flow diagram of an example process for a controlled substance diversion detection system in accordance with one or more aspects.

FIGS. 8-21 illustrate diversion scoring factors in accordance with one or more aspects.

FIG. 22 illustrates a flow chart of a manual diversion analytic process.

FIG. 23 illustrates a flow chart of a diversion analytic process in accordance with one or more aspects.

DETAILED DESCRIPTION

Figure 1:
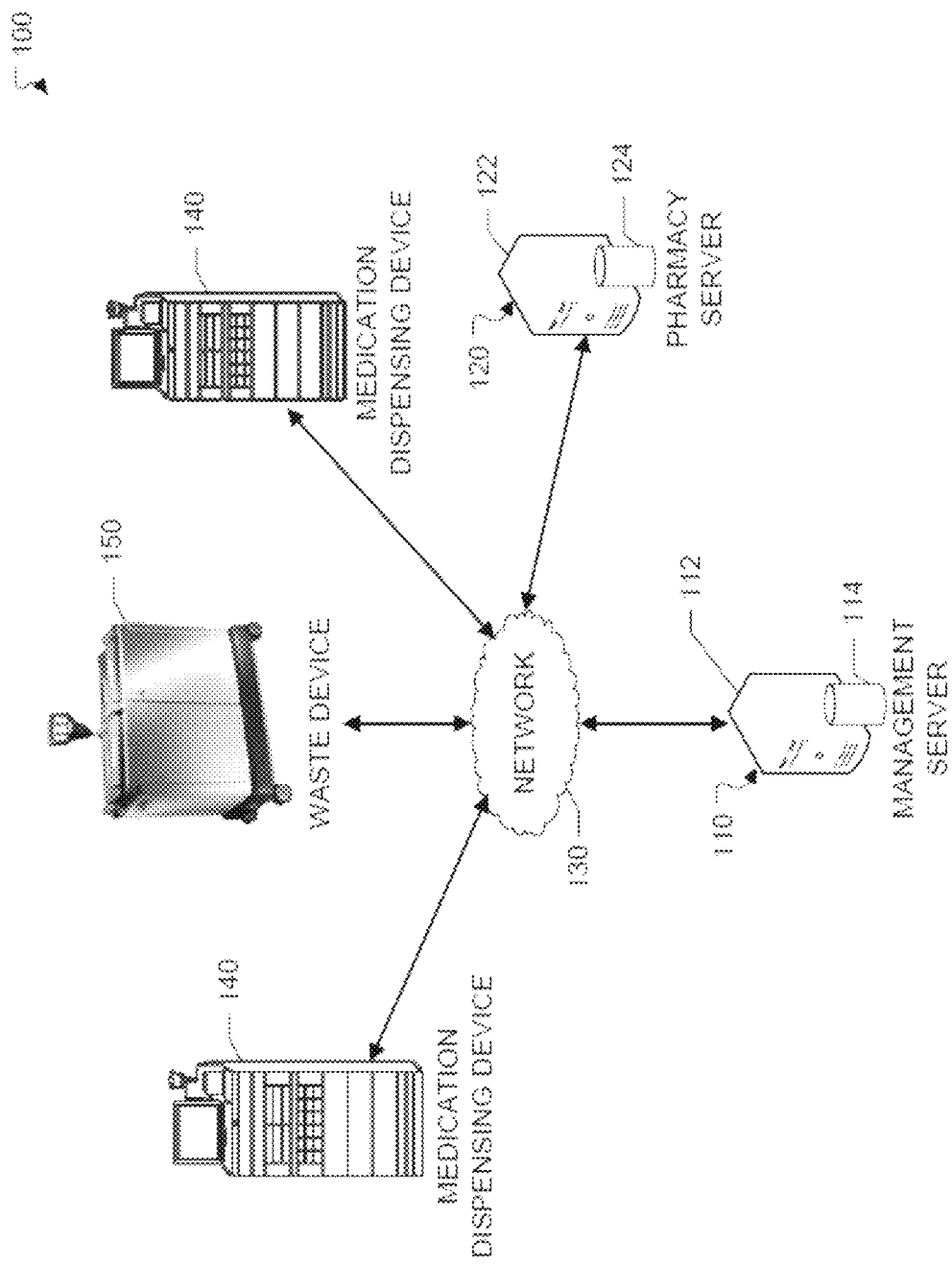
FIG. 1 illustrates an example system in which a controlled substance diversion detection system may be implemented in accordance with one or more embodiments.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure. In the referenced drawings, like numbered elements are the same or essentially similar. Reference numbers may have letter suffixes appended to indicate separate instances of a common element while being referred to generically by the same number without a suffix letter.

Controlled substances are groups of drugs that have in common that they are useful in the treatment of human disease, but also tend to be recreationally abused. Chapter 13 of Title 21 of the United States Code describes what drugs are controlled substances and entitles the Drug Enforcement Agency of the Department of Justice to classify and control these substances to prevent recreational abuse. That same law describes a classification scheme (Classes I-V) of controlled substances, in which Class I substances have a very high potential for abuse and addition and are unsuitable for therapeutic use, Class II drugs have a very high potential for abuse and are suitable for therapeutic use, down to class V, which require controls for purchase but do not require a prescription.

Controlled substances represent a minority of the population of therapeutic drugs, but represent a significant public health problem because of the patient-safety issues and criminal behavior engendered by recreational users, especially addicts, who may subordinate all other concerns to acquisition of a desired drug. Because most controlled substances have legitimate medical use, diversion and abuse of these substances by healthcare providers is of particular concern because diverters may have legitimate access to these substances as part of their work responsibilities which masks their drug diversion behavior, and drug diversion behavior may deny patients needed care or subject them to significant safety risk. Further, healthcare providers tend to work with each other within an expectation of mutual trust that predisposes diverters' colleagues to miss, or deny signs that one of their colleagues may be diverting controlled substances.

Drug seeking behavior is highly adaptive and diverters will constantly challenge any control system looking for a way to defeat it and acquire the drugs they seek. Also, drug diverters attempt to disguise their diversion as apparently legitimate use of controlled substances.

Current automated control systems have tightened security around controlled substances, but diversion still exists. Data captured by these systems has been shown to assist in identifying caregivers who are diverting drugs, but they only process a fraction of the available data, and serve only to stimulate what remains as a highly manual, and inferential forensic process that requires comparison of data from a large number of documents.

A substance is a "controlled substance" when it is determined to be abusable, has shown a pattern of abuse leading to dependency, and that abuse has been shown to create a risk to public health and safety. In many instances controlled substances have legitimate medical therapeutic uses, and so may be purchased, stored, dispensed and administered to patients during the treatment of injury or disease. Thus healthcare institutions may be required to maintain stores of controlled substances for these uses, and those stores may attract individuals who wish to use them for other purposes, leading to abuse. Those individuals may be employees of the healthcare institution itself. Thus, any organization that routinely uses controlled substances for valid therapeutic purposes can become a target for diversion.

Diversion of controlled substances by healthcare professionals can occur within any professions who have routine and appropriate access to these substances. The healthcare professionals with the most frequent access include physicians, nurses, pharmacists and pharmacy technicians. In general, when healthcare workers divert drugs, it is for personal use, and is symptomatic of addiction.

Diversion among nurses was first publicly acknowledged in 1984. Subsequently it was acknowledged that substance abuse among nurses varies between 2% and 18%. A 1998 report from the Cincinnati Police Pharmaceutical Division indicates the arrest of one healthcare professional every six days, among whom 70% were nurses. It is generally recognized that most drug diversion goes undetected, and that the problem is far more prevalent than published statistics represent. It is, in fact, questionable whether there are any reliable statistics on the prevalence of diversion by nurses. Part of the problem in gathering statistics is the level of denial associated with the problem.

Thus, while control systems limit the opportunity for diversion, they cannot entirely prevent it. They must, therefore, be accompanied by regular programs of analysis looking for patterns of drug acquisition that may indicate that diversion is occurring. Since this behavior is generally driven by personal dependence, diverters constantly stress any control systems intended to prevent such diversion by changing their diversion behaviors to attempt to defeat those controls.

The problem of diversion is not simply economic. For example, diversion activities may result in compromising the integrity, or sterility of sterile injectable medications, creating the possibility of treatment failure and/or nosocomial infections. Diversion activities may also result in recreational use of controlled substances while caring for patients, resulting in compromised medical judgment, poor techniques, oversights, and inadequate documentation, all of which could lead to medical error. In addition, diversion activities may result in under-treatment of patient pain, resulting in loss of sleep, agitation, and other discomforts for the patient. Also, diversion activities may result in placing additional workload burdens on companion caregivers, increasing their likelihood of making a mistake. Thus, controlled substance diversion by healthcare personnel therefore represents a public health risk that is desirable to be identified and controlled.

In general, healthcare providers divert controlled substances by seeming to acquire those substances for legitimate purposes, and then redirecting them for personal use. For example, a number of references may describe signs and symptoms that a healthcare worker is diverting drugs.

Excessive use compared with other caregivers in the same area

Excessive amounts of wasting compared to other caregivers in the same area. For example, when a caregiver prepares a dose of a controlled substance that will consume only a portion of that controlled substance medication product (e.g., ½ tablet, a portion of a prefilled syringe or single-use vial), that caregiver is required to destroy the remaining portion and a have that destruction witnessed by another caregiver. Such destruction is generally referred to as "wasting."

A tendency to use higher doses for any particular patient in comparison to other caregivers A tendency to omit waste co-signature documentation, or significantly delay that documentation A tendency to always have waste documented by another high-using caregiver Increases in inventory discrepancies compared to other caregivers Unusual removal patterns inconsistent with ordered therapy Evidence of physical tampering with container packaging noticed during count. For example, count is an inventory verification process in which two caregivers physically review the amount of controlled substances inventory.

Evidence that patients are not experiencing expected pain relief while under the care of the suspected caregiver (may require additional data sources)

Evidence that the caregiver is removing drugs, documenting waste, or otherwise interacting with the system when not scheduled to work (may require additional data sources).

A sudden change (usually an increase) in a caregiver's controlled substances usage for patients Additionally, there are additional behavioral signs and symptoms that may be used for detection of diversion.

Illness and absenteeism above the normal rates

Frequent or prolonged absence from the work area when on duty

Volunteering for overtime, or to care for patients with excessive need for pain medication Volunteering to "carry the keys." This refers to controlled substance inventory kept within a locked cabinet that requires a specified caregiver to be the custodian of the keys to that cabinet and to be interrupted as needed to let other caregivers acquire controlled substances for their patients.

Performance declines as represented both by objective performance and complaints from co-workers Increasing professional isolation Poor or incomplete record-keeping Personality changes and deterioration in appearance and hygiene Defensive behavior; inability to accept criticism Visiting patients when not on duty Current tools typically focus on comparing frequency of drug dispenses, drug wasting behavior, and acquisition timing from automated dispensing cabinets as a primary strong indicator of likelihood of diversion, using a standard deviation of the mean across caregivers for a specific patient population as the primary indicator. It is typically up to the system user to set the boundaries above which an individual becomes "suspicious." High use isn't necessarily an indictment, but it is an indicator that more research is needed. Discussions with those interested in this problem (primarily nurse investigators) indicates that the process of investigating and dealing with a diverter only starts with these current tools, and relies on very labor-intensive manual investigation methods to finally reach a conclusion.

For example, the forensic tools available to manage this process are very crude, and focus on a single strong indicator, such as statistically significant overuse of controlled substances to patients as indicated by various automated logs. This method, while better than nothing, still leaves a large population that requires arduous winnowing to identify actual diverters, and often fails to capture more sophisticated diverters who know how to "fly under the radar." Also, diversion by caregivers in a hospital setting presents differently than diversion from a pharmacy supply, which in turn presents differently from diversion of anesthesia controlled substance supplies.

As evidenced by the much more extensive list of signs and symptoms, it is desired that a properly constructed system build a much more robust picture of individuals who might be diverting, especially if such a system is configured to acquire key information from other programs, such as the electronic medical record. Further, since the goal of the diverter is to mask the diversion behind the appearance of normal patient care behavior, it is likely that there are more successful diverters who would be unlikely to trip consumption limits, but who might show other behaviors that they do not realize are being observed and tracked.

Provided is a system configured for a more multi-axial approach to measurement of potential diversion based on two or three strong factors (e.g., factors weighted as strong factors), for which further adjacencies are analyzed in an effort to better identify and target those whose total behavior picture suggests diversion activity. Specifically, the use of gross usage, suspicious wasting behavior, and elevated occurrence of discrepancies may serve as primary triggers, which may then be qualified by weaker factors (e.g., factors weighted as weak factors) focused on those suspicious providers. For example, the system may include a single computer and/or a network of computers to provide organized forensic information, while a portion of the system may include automated dispensing cabinets that log specific mechanical activity and provide forensic indicators based on the automated dispensing cabinets.

The system may be configured to build up a score on the strong factors, and then invoke a series of automated investigations, primarily around patient records for the patients being cared for by suspected diverters. The system may also be configured to build up a series of factor scores around each measure summing to a total diversion score. For example, algorithms may be based on data sets containing known diversion activity. Further, the system may be configured to provide a summary-level display as described in further detail below (see, e.g., FIG. 2).

Some disclosed embodiments include a system that uses data inputs from automated medication dispensing equipment, nurse charting systems, nurse scheduling systems, electronic medical records and other software found in healthcare systems that may be used to detect and investigate individuals who appear to be diverting controlled drugs for personal use or resale.

For example, the system may start with a series of signals from, for example, medication dispensing devices, pharmacy servers, and/or waste devices that provide data associated with a health care provider obtaining a medication such as a controlled medication. The received signals may be related to various factors related to diversion to be evaluated. The received signals may be used to independently statistically evaluate each factor across the appropriate patient population to build up a quantitative picture of those caregivers who are suspected to be diverters, and then rank each suspect by the presence and strength of each of those factors. Strength of a factor may be related primarily to the ease of independent detection of an associated signal and/or an analysis based on a data set of known diversion activity, for example. The output may be a scorecard where those caregivers who have the highest number of factors with the highest strength are highlighted for further investigation, and where the forensic data that led to this analysis is available (e.g., in a clickable-link table) for drill-down analysis. The system may monitor a series of relationships between caregivers (e.g., nurses and physicians) and their use of controlled substances across specified patient populations to identify and/or score strong and weak factors.

Such factors, for example, may relate to over-use of controlled substances (e.g., compared to a peer-based norm for a patient care area) and over-use of containers, part of whose contents must be wasted (e.g., compared to a peer-based norm for a patient care area). Other factors may relate to failure to obtain co-signatures for waste, prolonged time between use and documentation of waste, and a tendency to have waste activities cosigned by other individuals who are also suspected of being diverters. Still other factors may relate to over medication of particular patients (e.g., compared to the amount of medication used by peers in the care of the same patient) either by dose or frequency or both, failure to chart pain scores as a result of medication, and acquisition of oral medication for a patient that is listed as a nothing-by-mouth or nil per os (NPO) patient. Other factors may relate to patient complaints of not getting relief of pain, dose administration timing versus vend timing, and other patient record data. Further factors may relate to prolonged patient recovery times (e.g., for anesthesia drugs) and high discrepancy rate (e.g., for anesthesia or pharmacy drug supplies). Yet other factors may relate to caregiver vending activity when not scheduled for duty, caregiver vending activity when not on an assigned floor, and switching back and forth between automated dispensing cabinets.

Some aspects of the system may quantify a score for each factor based on extent or frequency of signals for the caregiver being reported, construct a profile for each suspected caregiver based on the accumulated factor scores, and compute a total diversion score. The system may display a list of suspects ordered by diversion score showing which factors are present for each caregiver, and the strength of the each factor by caregiver with the ability to drill down on each score until a detailed listing of related transactions can be reviewed.

To monitor the appropriate signals, the system may review transactional data from automated dispensing cabinets associated with a particular patient care area to which nurses maybe assigned, anesthesia record-keeping systems, electronic patient records, nurse scheduling systems, pharmacy scheduling systems, surgical case reporting, nurse charting systems, medication administration record systems and/or pharmacy perpetual inventory (e.g., CII Safe). The system may be configured to monitor all of these signals, or any combination of factors, for example. For example, some information may reside in operational logs that are maintained by dispensing equipment that automatically date stamp, time stamp, and/or user stamp every transaction, thereby eliminating problems that are caused by a manual process. As a case in point, a manual paper system provides a much easier diversion environment because the date/time information on the paper system is whatever the user wrote on the documents, which is often completed long after the originating dispensing activity.

FIG. 1 illustrates an example system 100 in which a controlled substance diversion detection system may be implemented in accordance with one or more embodiments. Not all of the depicted components may be required, however, and one or more embodiments may include additional components not shown in the figure. Variations in the arrangement and type of the components may be made without departing from the spirit or scope of the claims as set forth herein. Additional, different or fewer components may be provided.

System 100 may be a hospital network, a network associated with a portion of a hospital or other healthcare facility, a network that includes multiple hospitals and/or other healthcare facilities. System 100 may include a number of medical devices, such as one or more medication dispensing devices 140 and/or one or more waste devices 150, that may be communicably coupled to one another and to one or more of a management server 110 and/or a pharmacy server 120, such as by the network 130. In addition, there may be a number of other devices connected to the network 130, such as additional medical devices, additional servers, computing devices, mobile devices, etc.

The network 130 may be a public communication network (such as the Internet, cellular data network, dialup modems over a telephone network) or a private communications network (such as private local area network ("LAN"), leased lines). The network 130 may also include, but is not limited to, any one or more of the following network topologies, including a bus network, a star network, a ring network, a mesh network, a star-bus network, a tree or hierarchical network, and the like. The connections may be wired or wireless.

The one or more medication dispensing devices 140 may be devices that store and dispenses medications, such as at a nurse's station. In one or more embodiments, one or more of the medication dispensing devices 140 may be a Pyxis MedStation™ Automated Dispensing Machine (ADM). The waste devices 150 may be devices that accept and store wasted medications, e.g., excess medications, from healthcare professionals and track the amount of medications wasted by healthcare professionals. In one or more embodiments, one or more of the waste devices 150 may be a Pyxis EcoStation™ system.

In one or more embodiments, one or more of the medication dispensing devices 140 and/or the waste devices 150 may include a processing device, such as a processor, and a memory. The processing device executes computer instructions stored in the memory, such as to implement one or more processes of the subject controlled substance diversion detection system. In one or more examples, the computer instructions may be stored on a non-transitory computer-readable medium. In one or more embodiments, a medication dispensing device 140 and a waste device 150 may be combined in a single device.

In one example, the management server 110 and/or the pharmacy server 120 may be single computing devices such as computer servers and/or the management server 110 and the pharmacy server 120 may be a single machine. In another example, the management server 110 and/or the pharmacy server 120 may represent one or more separate computing devices (such as a cloud of computers and/or a distributed system) that are communicatively coupled, such as communicatively coupled over the network 130, that collectively, or individually, perform one or more server-side functions. In this example, the one or more computing devices of the management server 110 and/or the pharmacy server 120 may be geographically collocated and/or disparately located. The management server 110 and/or pharmacy server 120 may be coupled with various databases, storage services, or other computing devices.

In one or more embodiments, the management server 110 includes a processing device 112 and a data store 114. The processing device 112 executes computer instructions stored in the data store 114, such as to implement one or more processes of the subject controlled substance diversion detection system. In one or more examples, the data store 114 may store the computer instructions on a non-transitory computer-readable medium. In one or more embodiments, the pharmacy server 120 includes a processing device 122 and a data store 124. The processing device 122 executes computer instructions stored in the data store 124, such as to implement one or more processes of the subject controlled substance diversion detection system. In one or more examples, the data store 124 may store the computer instructions on a non-transitory computer-readable medium. In one or more embodiments, the management server 110 and/or the pharmacy server 120 may be, or may include, the electronic system 8000 discussed below with respect to FIG. 24.

In operation, one or more of the medication dispensing devices 140 may implement one or more aspects of the subject controlled substance diversion detection system, such as by performing one or more of the example processes that are discussed further below with respect to FIGS. 2-23. In addition, one or more of the management server 110 and/or the pharmacy server 120 may implement one or more aspects of the subject controlled substance diversion detection system, such as by performing one or more of the example processes that are discussed further below with respect to FIGS. 2-23.

Figure 2:
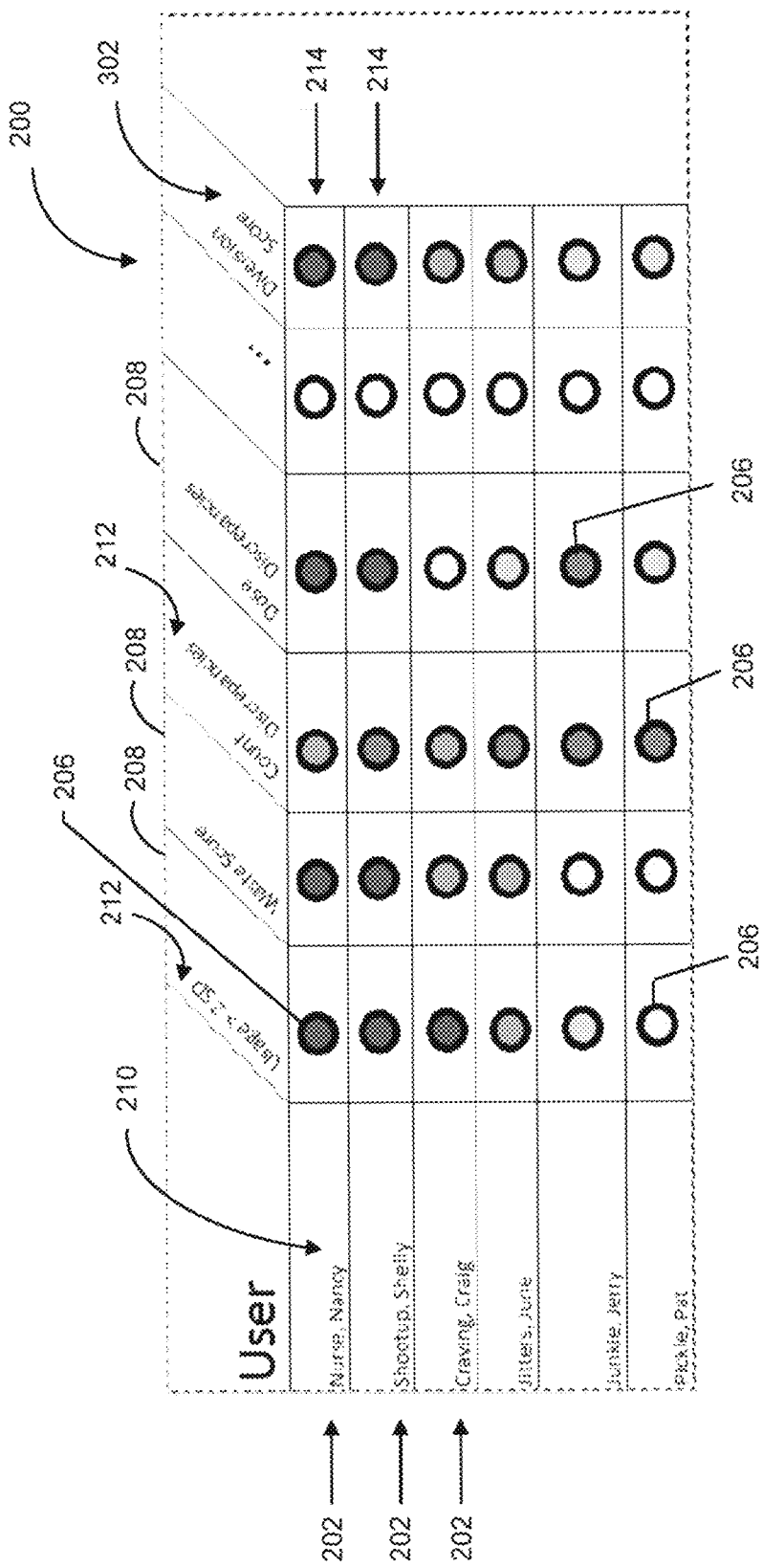
FIG. 2 illustrates an example summary level display of a controlled substance diversion detection system that may be implemented in accordance with one or more embodiments.

FIG. 2 illustrates an example summary level display 200 that may be generated and provided (e.g., by management server 110 and/or pharmacy server 120). As shown, summary display 200 may include of a listing of top diverter suspects 202. A listing of factors 212 and associated factor score indicators 206 related to controlled substance diversion may be listed along with the names of the suspected diverters 202. In some implementations, the weight or ranking of the factors and factor scores may be visually highlighted by color codes, shading, numbers and the like. For example, a weighting scheme may be determined from data analysis of a data set containing transactions by known diverters.

As shown in FIG. 2, summary display 200 may include a grid listing the top potential diverters 202 (e.g., the top 6 potential diverters, the top 10 potential diverters, or any suitable number of top potential diverters) in descending order by total diversion score 302. For each potential diverter 202, a series of graphic indicators 206 (e.g., factor score indicators), one for each factor score, may be provided indicating the strength of that factor 212 and/or the value of the factor score. Summary display 200 may be provided to facilitate identification of potential diverters 202, and to provide easy access to further information about each potential diverter 202 for a subsequent investigation and confirmation of actual diverters. Confirmation of a diverter may be provided by catching the person in the act of diversion (e.g., in possession of stolen controlled substances) or by obtaining a confession on questioning, for example. Confirmation of diversion may provide the basis for discipline or criminal prosecution of the diverter.

As noted, summary display 200 may be arranged to provide access to additional information associated with each factor 212 for each potential diverter 202. For example, clicking on the name of the potential diverter 202 may cause the system to display reports on that potential diverter's behavior. Clicking on a column header listing 208 for a particular factor 212 may cause different reports to display the statistics around that particular diversion behavior. Clicking on a particular graphic indicator 206 in a particular row 214 may cause display of a report of summary individual indicator scores for that potential diverter for that diversion behavior indicator. From any of these summary display access points, the user may ultimately drill down to individual transactions associated with a potential diverter. Also, the system may be configured to provide links to a series of documents describing a profile or dossier of the potential diverter with instructions on how to take the investigation forward, and what kinds of diversion evidence or indicators to look for. For example, such instructions might include characteristics of addiction to the controlled substances a potential diverter seems to be taking, as well as general information about the behavioral characteristics of diverters.

FIGS. 3-7 are flow diagrams illustrating example processes for a controlled substance diversion detection system.

More particularly, FIGS. 3-7 illustrate example processes (also described in further detail below in connection with FIGS. 8-21) for determining factor scores that can be used and/or combined to determine a diversion score. As described above in connection with FIG. 2, the determined diversion scores can be used to provide a ranked list of potential diverters (see, e.g., summary display 200) that includes links to information that can be navigated and used to identify actual diverters. The factor scores of FIGS. 3-8 (e.g., a usage score, a waste score, a scheduling score, a dose score, and discrepancy and hardware scores for FIGS. 3-8 respectively) can be determined for each of one or more health care providers (e.g., nurses), in part, based on signals received from one or more medication dispensing devices that automatically monitor dispensing of controlled medications and/or other substances therefrom.

Figure 3:
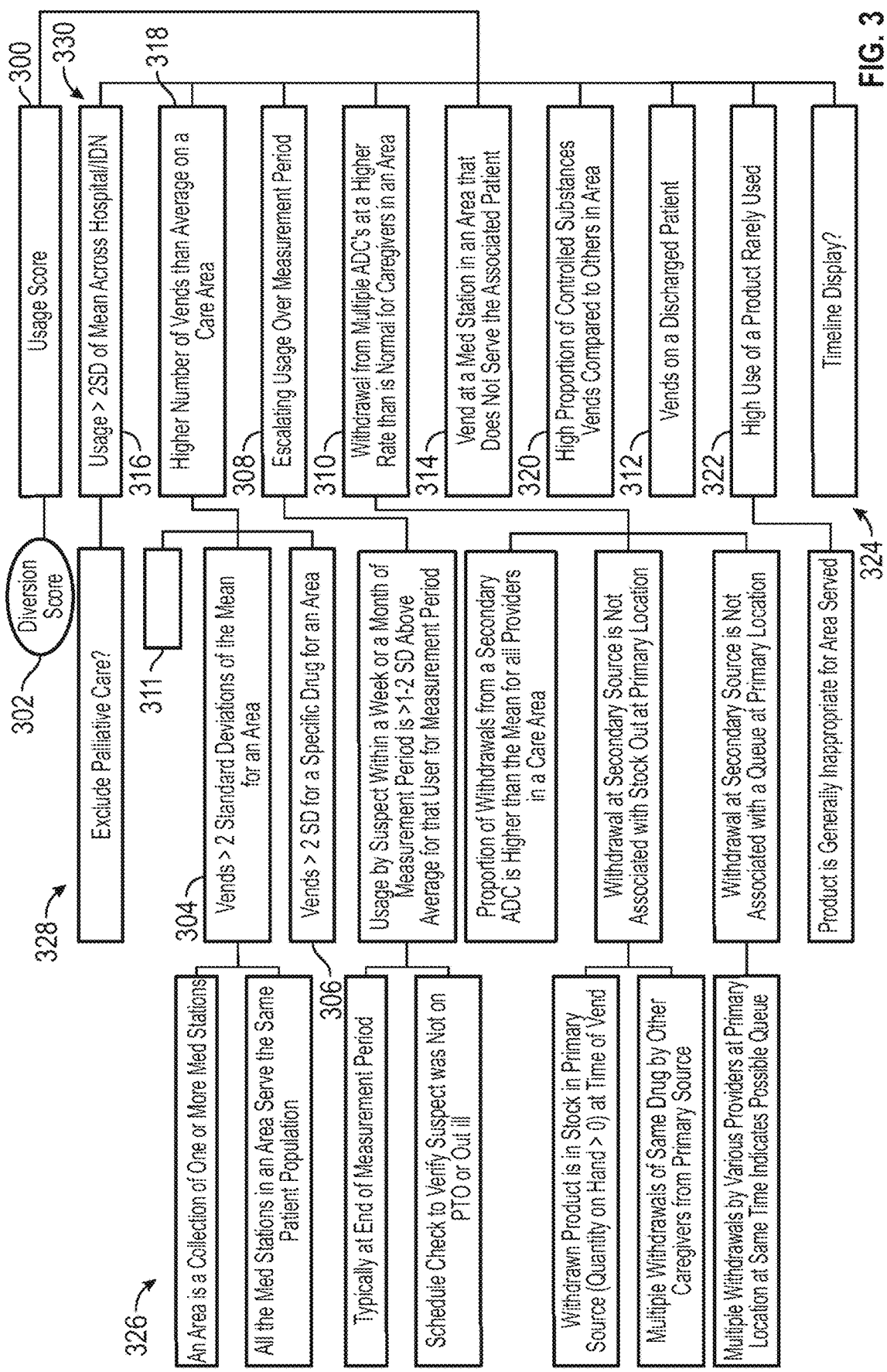
FIG. 3 illustrates a flow diagram of an example process for a controlled substance diversion detection system in accordance with one or more aspects.

In the example of FIG. 3, an example process for determining a usage score is illustrated. As shown, total usage score 300 (which may be used to determine diversion score 302) may be determined based on a combination of usage factors 330. Usage factors 330 may include escalating usage of a measurement period 308, distributed automatic dispensing cabinet (ADC) usage 310 (e.g., at a rate that is higher than normal for caregivers in an area), vend for a discharged patient 312, vend at an ADC that does not normally serve that patient 314, usage greater than two standard deviations (SD) above the mean usage 316 across a hospital or other integrated delivery network (IDN) such as a nationwide IDN, higher number of vends than average on a care area 318, high proportion of controlled substances vends compared to others in an area 320, high usage of a product rarely used 322, and/or other usage factors (see, e.g., FIGS. 12-15). In some implementations, a timeline display 324 of usage may be provided. As shown in FIG. 3, various usage flags 328 such as vends for a care area 304 and vends of a specific drug for a care area 306 may be combined to determine one or more of usage factors 330. Placeholder flags 311 may also be provided (e.g., to accommodate flags or factors identified by the system using advanced analytics as being indicative of diversion activities). Various input parameters and definitions 326 may also be provided (e.g., stored by management server 110 and/or input by a user). Parameters and definitions 326 may be used and/or combined to guide and inform usage flags 328, in some implementations.

Figure 4:
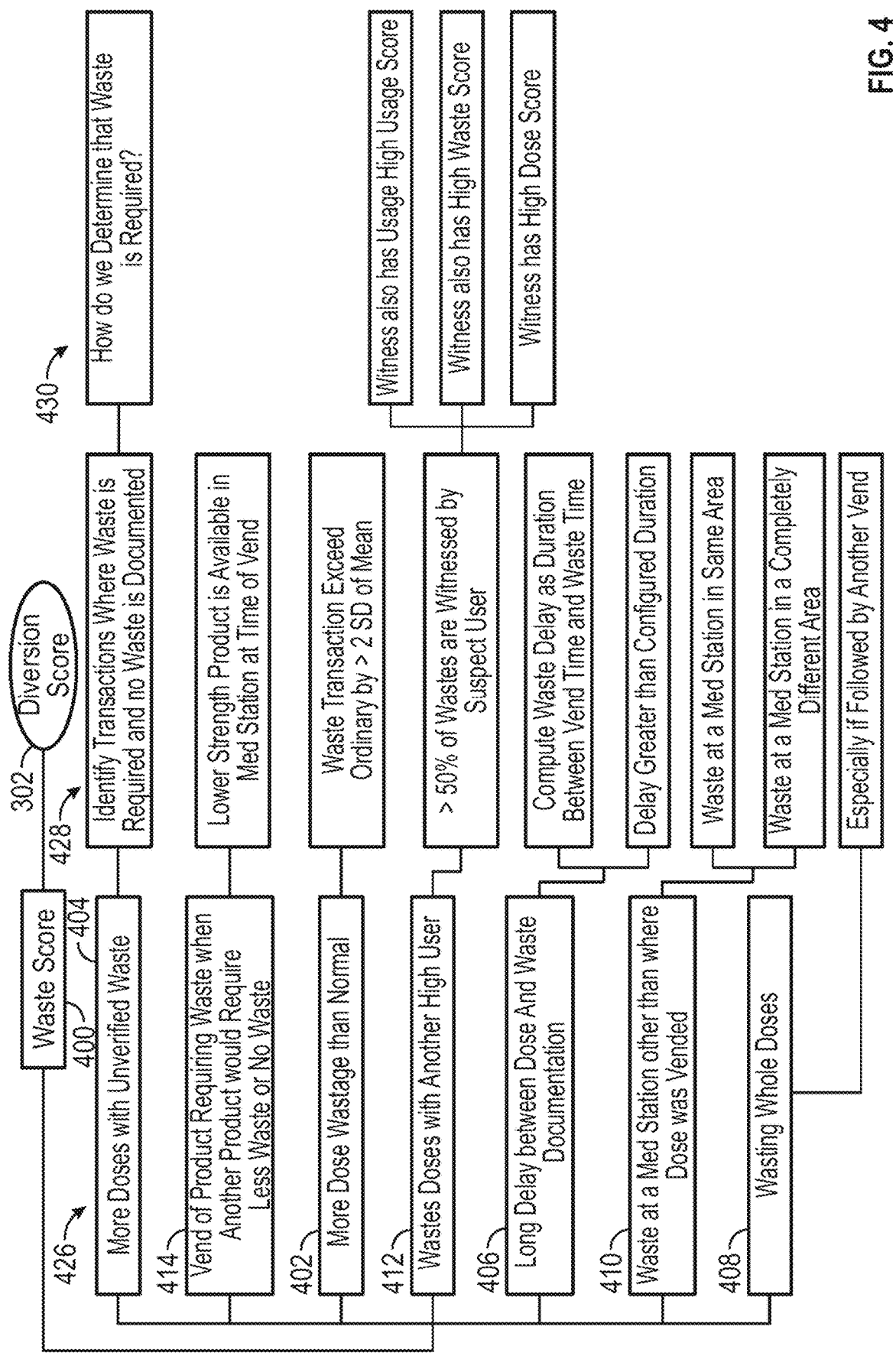
FIG. 4 illustrates a flow diagram of an example process for a controlled substance diversion detection system in accordance with one or more aspects.

In the example of FIG. 4, an example process for determining a waste score is illustrated. As shown, total waste score 400 (which may be used to determine diversion score 302) may be determined based on a combination of waste factors 426. Waste factors 426 may include more waste than normal 402, unverified waste 404, long delays between vend and waste 406, waste of whole doses 408, vend and waste performed at different med stations 410, waste doses with another potential abuser 412, and vends of higher dose product that generate higher waste when exact or smaller doses are available 414 and/or other waste factors (see, e.g., FIGS. 8-11). As shown in FIG. 4, various waste flags 428 may be used and/or combined to determine one or more of waste factors 426. Various input parameters and definitions 430 may also be provided (e.g., stored by management server 110 and/or input by a user). Parameters and definitions 430 may be used to guide and inform waste flags 428, in some implementations.

Figure 5:
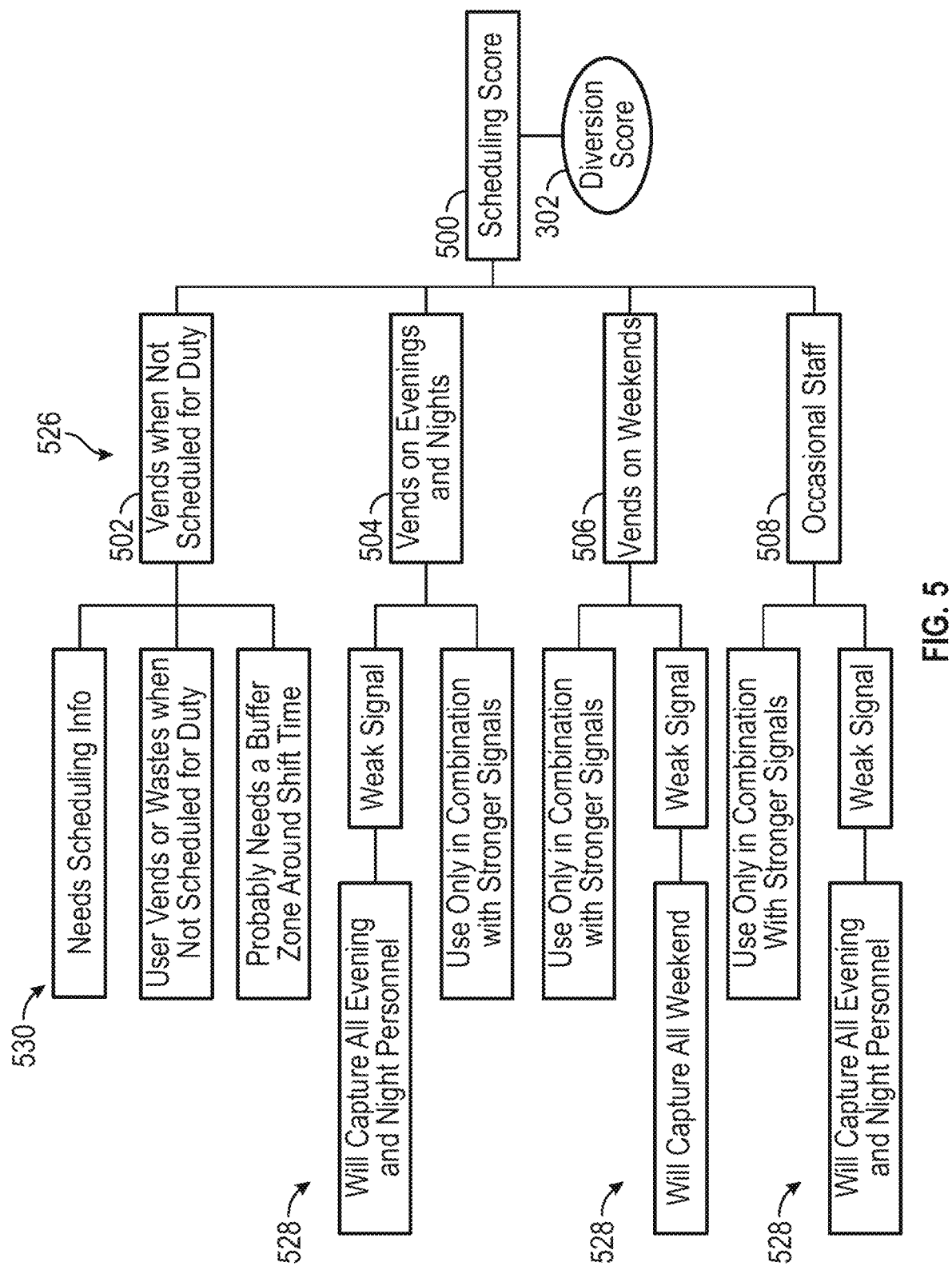
FIG. 5 illustrates a flow diagram of an example process for a controlled substance diversion detection system in accordance with one or more aspects.

In the example of FIG. 5, an example process for determining a scheduling score is illustrated. As shown, total scheduling score 500 (which may be used to determine diversion score 302) may be determined based on a combination of scheduling factors 526. Scheduling factors 526 may include vends when not on duty 502, vends on evenings and nights 504, occasional staff 508, weekend vends 506 and/or other scheduling factors (see, e.g., FIG. 21). As shown in FIG. 5, various scheduling flags 530 may be used and/or combined to determine one or more of scheduling factors 526. Various input parameters and definitions 528 may also be provided (e.g., stored by management server 110 and/or input by a user). Parameters and definitions 528 may be used to guide and inform scheduling flags 530, in some implementations.

Figure 6A:
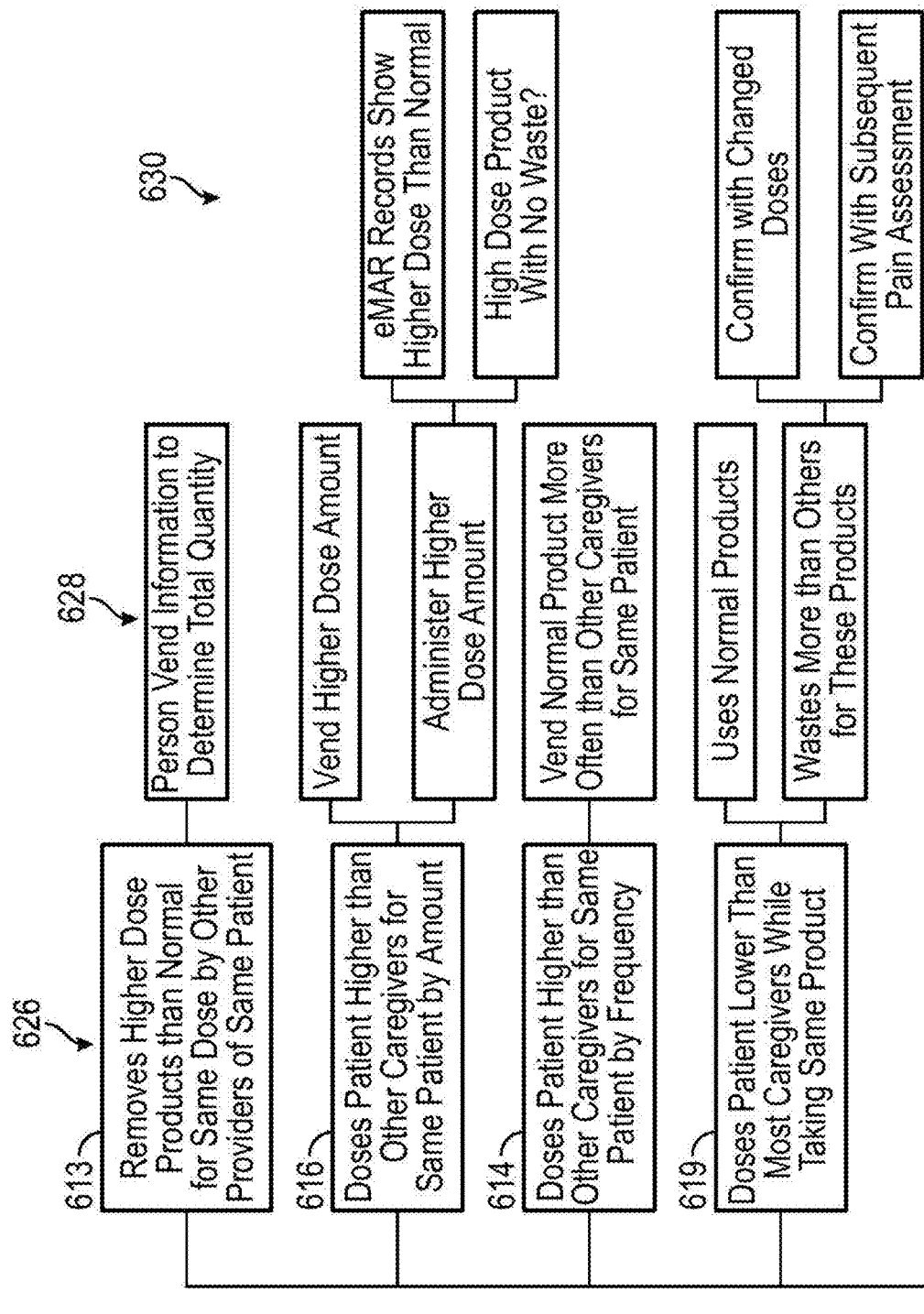
Figure 6B:
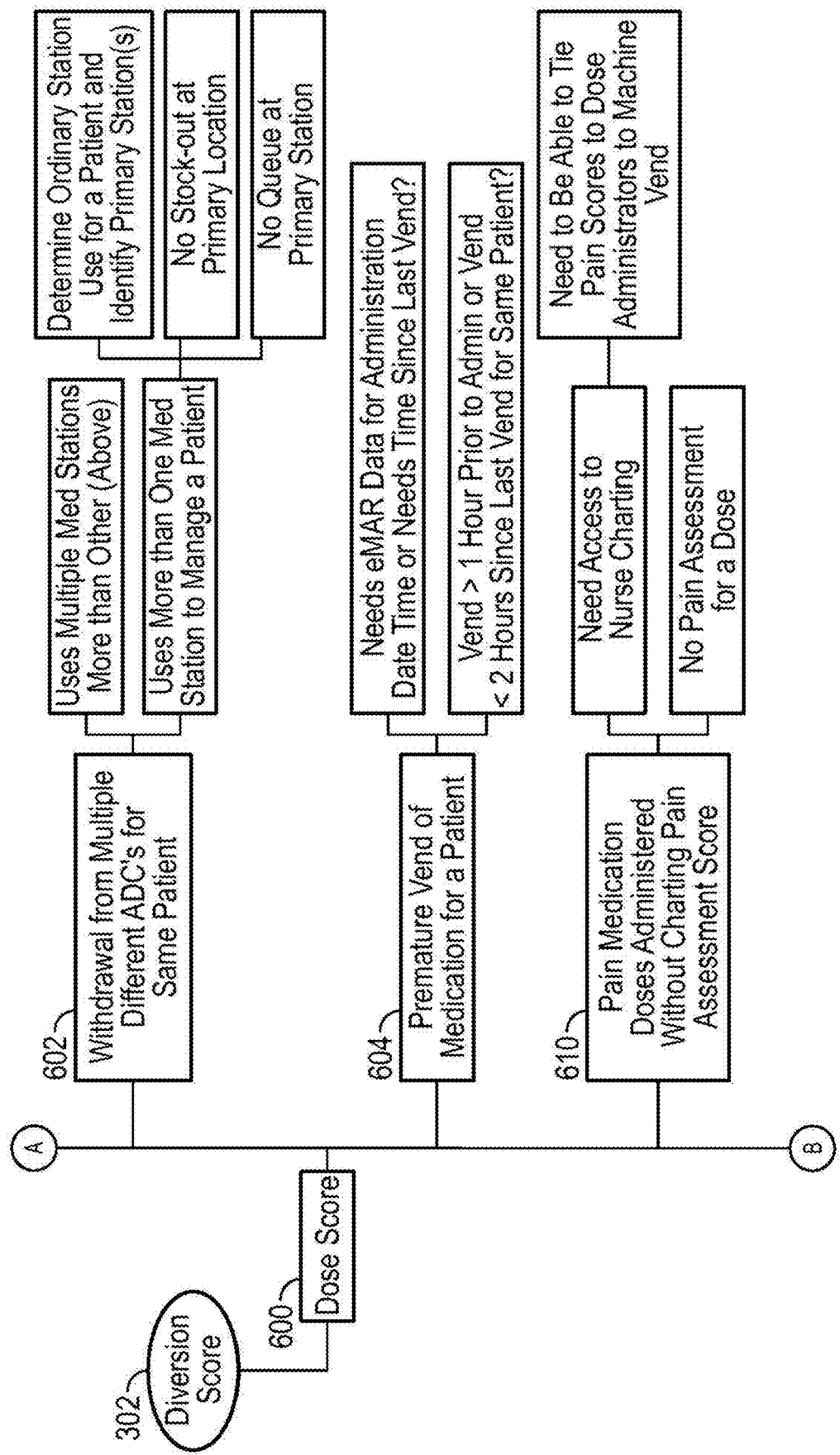

In the example of FIGS. 6A-6C, an example process for determining a dose score is illustrated. As shown, total dose score 600 (which may be used to determine diversion score 302) may be determined based on a combination of dose factors 626. Dose factors 626 may include removes higher dose products than normal for the same dose by other providers for the same patient 618, higher dose at same frequency 616, doses higher than vended by other caregivers by frequency 614, doses patient less and wastes more 619, withdrawal from multiple ADCs for same patient 602, premature vend 604, vend of oral medication for nil per os (NPO) patient 606, vend of more doses than permitted in the order 608, pain medication given without pain assessment 610, failure of dose to manage pain 612, and/or other dose factors (see, e.g., FIGS. 16-20). As shown in FIGS. 6A-6C, various dose flags 628 may be used and/or combined to determine one or more of dose factors 626. Various input parameters and definitions 630 may also be provided (e.g., stored by management server 110 and/or input by a user). Parameters and definitions 630 may be used to guide and inform dose flags 626, in some implementations.

Figure 7:
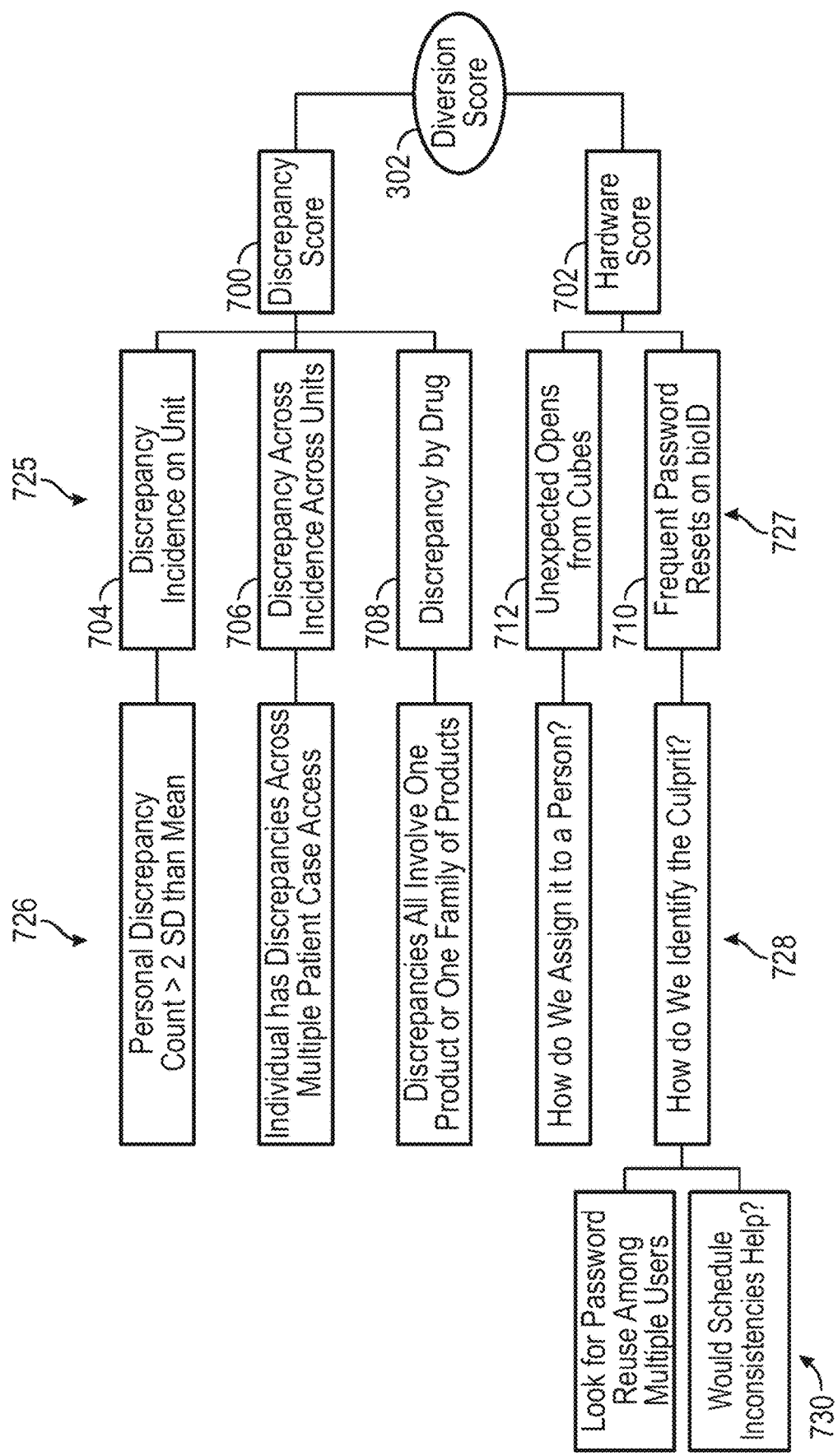
FIG. 7 illustrates a flow diagram of an example process for a controlled substance diversion detection system in accordance with one or more aspects.
Figure 9:
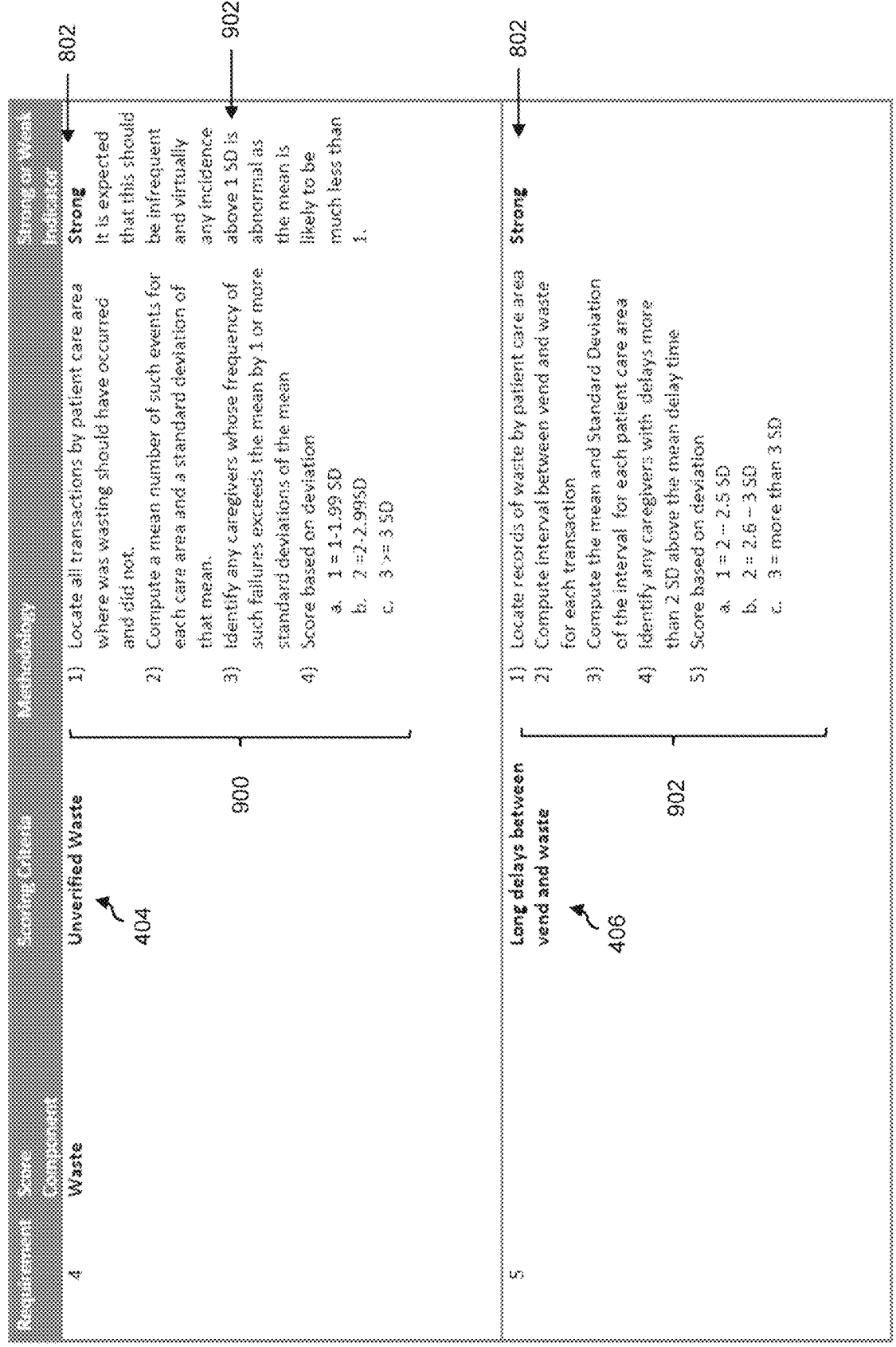
Figure 10:
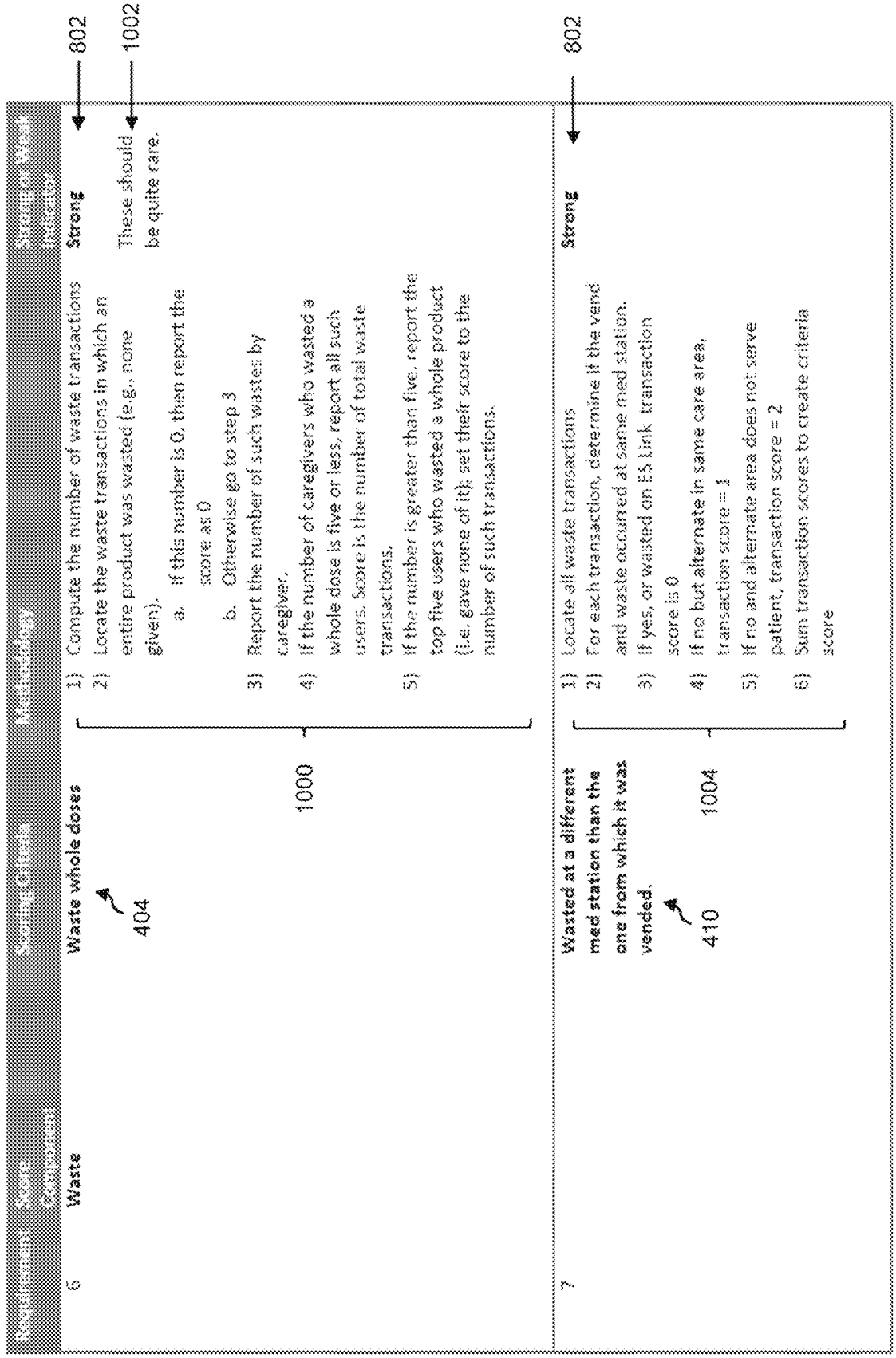
Figure 11:
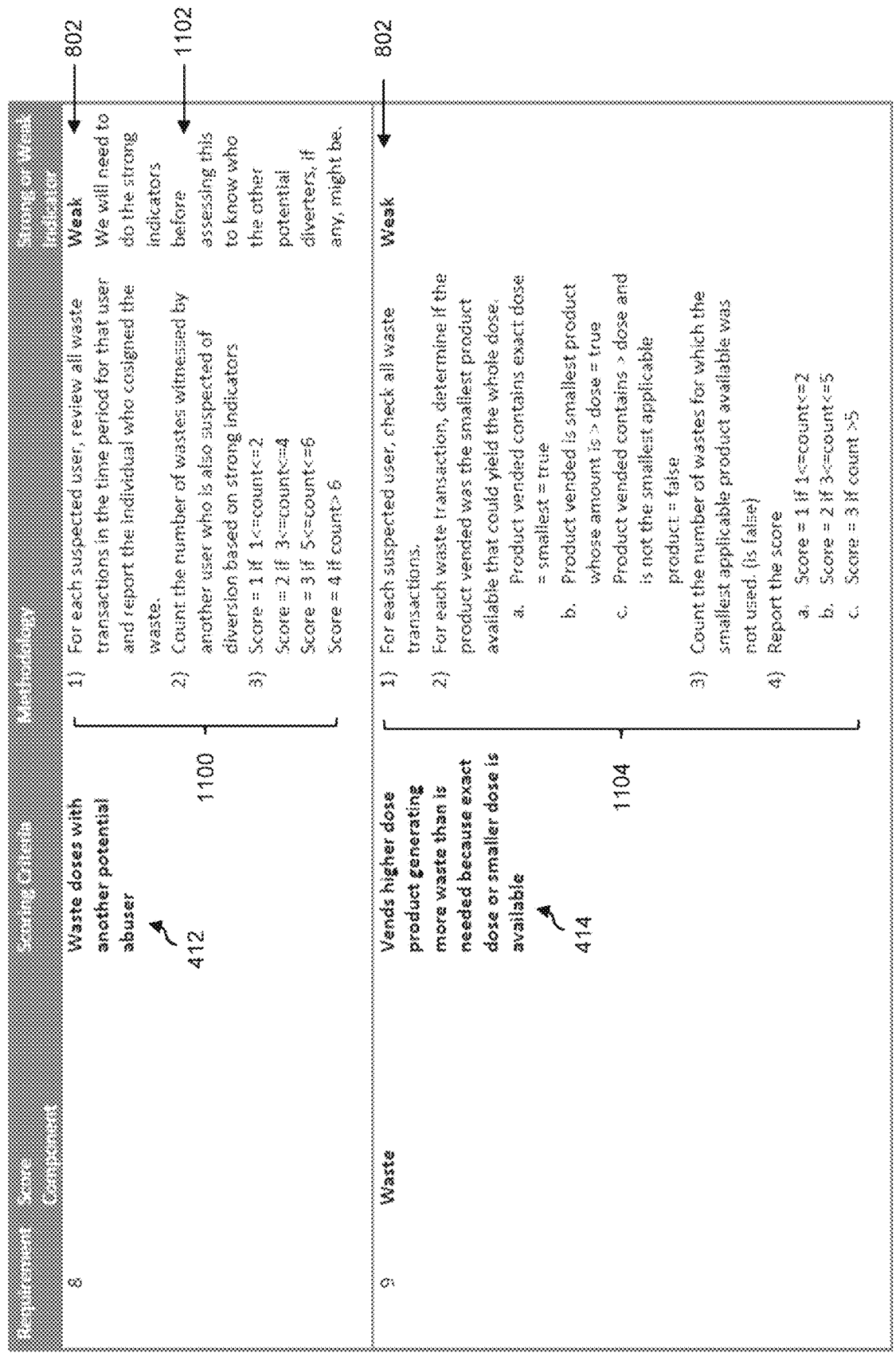

In the example of FIG. 7, an example process for determining a discrepancy score is illustrated. As shown, total discrepancy score 700 (which may be used to determine diversion score 302) may be determined based on a combination of discrepancy factors 725. Discrepancy factors 725 may include discrepancy incidence on unit 704, discrepancy across incidence across units 706, discrepancy by drug 708 and/or other discrepancy factors. As shown in FIG. 7, various discrepancy flags 726 may be used and/or combined to determine one or more of discrepancy factors 725.

FIG. 7 also shows an example process for determining a hardware score. As shown, total hardware score 702 (which may be used to determine diversion score 302) may be determined based on a combination of hardware factors 727. Hardware factors 727 may include frequent password resets on a biological identification (bioID) system 710, unexpected opens from cubes 712, and/or other discrepancy factors. As shown in FIG. 7, various hardware flags 728 may be used and/or combined to determine one or more of hardware factors 727. Various input parameters and definitions 730 may also be provided (e.g., stored by management server 110 and/or input by a user). Parameters and definitions 730 may be used to guide and inform hardware flags 728, in some implementations.

Any combination of the elements or factors shown in FIGS. 3-7 may be used to determine the corresponding scores. Further, any combination of the usage, waste, scheduling, dose, discrepancy and hardware factor scores may be used (e.g., summed or otherwise combined) to determine a diversion score (e.g., a diversion score for a particular person). Additional factors, elements or scores may also be used to determine a total diversion score for a particular person, for example. FIGS. 8-21 provide additional details for determination of the diversion score and factor scores of FIGS. 3-7, including additional factors that may be used in some cases, and processes that may be performed for determining each factor score.

For example, FIG. 8 includes a process 800 for generating and providing a summary display such as summary display 200 of FIG. 2. In particular, process 800 includes combing (e.g., summing) one or more factor scores (e.g., a factor score for one or more of waste, usage, dose hardware, scheduling, and/or discrepancy) to generate a total diversion score for each provider. Process 800 may also include reporting the top n providers in descending order by score, wherein n is a configurable number of potential diverters, configurable at a site level, hospital level, ward level, network level, national level, or global level. Reporting the top n providers may include providing summary display 200 with clickable links for obtaining additional information for each potential diverter in each category.

Prior to combining the factor scores in process 800, each factor score may be determined (e.g., by management server 110) using a corresponding process for that factor score as illustrated in FIGS. 8-21.

For example, FIG. 8 also shows a process 804 that may be performed for determining a total waste score 400. Total waste score 400 may be determined using factors in a waste category 801. Each factor may have a strength 802 (e.g., strong or weak). In some cases (see, e.g., comments 902 and 1002 respectively of FIGS. 9 and 10), strength 802 may be accompanied by a guidance note related to the factor associated with that strength.

As shown in FIGS. 8-11, factors related to waste category 801 may be analyzed, such as more waste than normal 402, unverified waste 404, long delays between vend and waste 406, waste of whole doses 408, vend and waste performed at different med stations 410, waste doses with another potential abuser 412, and vends of higher dose product that generate higher waste when exact or smaller doses are available 414. Waste factors 404, 406, 408, 410, 412, and 414 may be determined, respectively using processes 804, 806, 900, 902, 1000, and 1004. Any combination of these waste factors 404, 406, 408, 410, 412, and 414 may be used to provide total waste score 400 using process 804.

Figure 12:
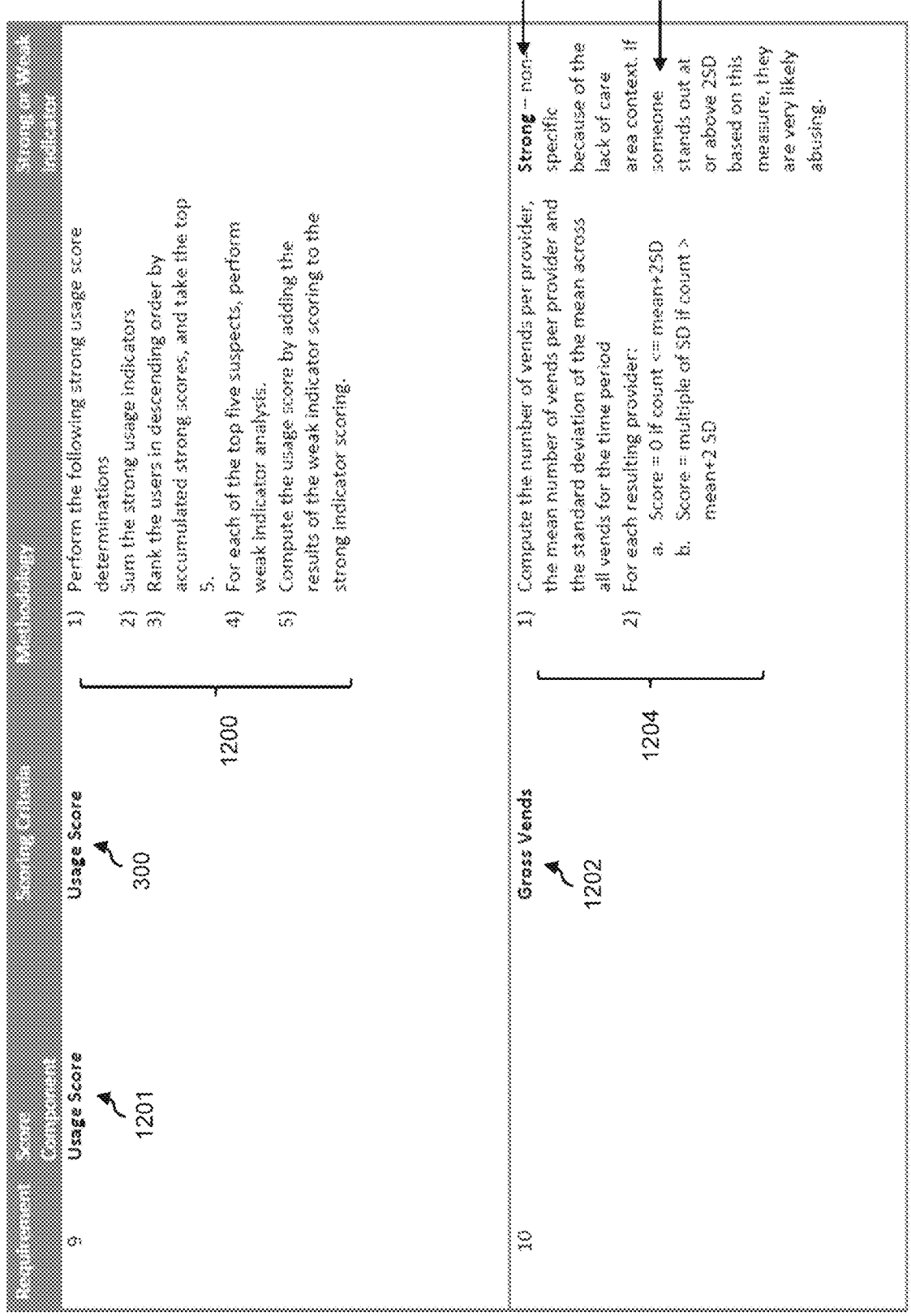
Figure 13:
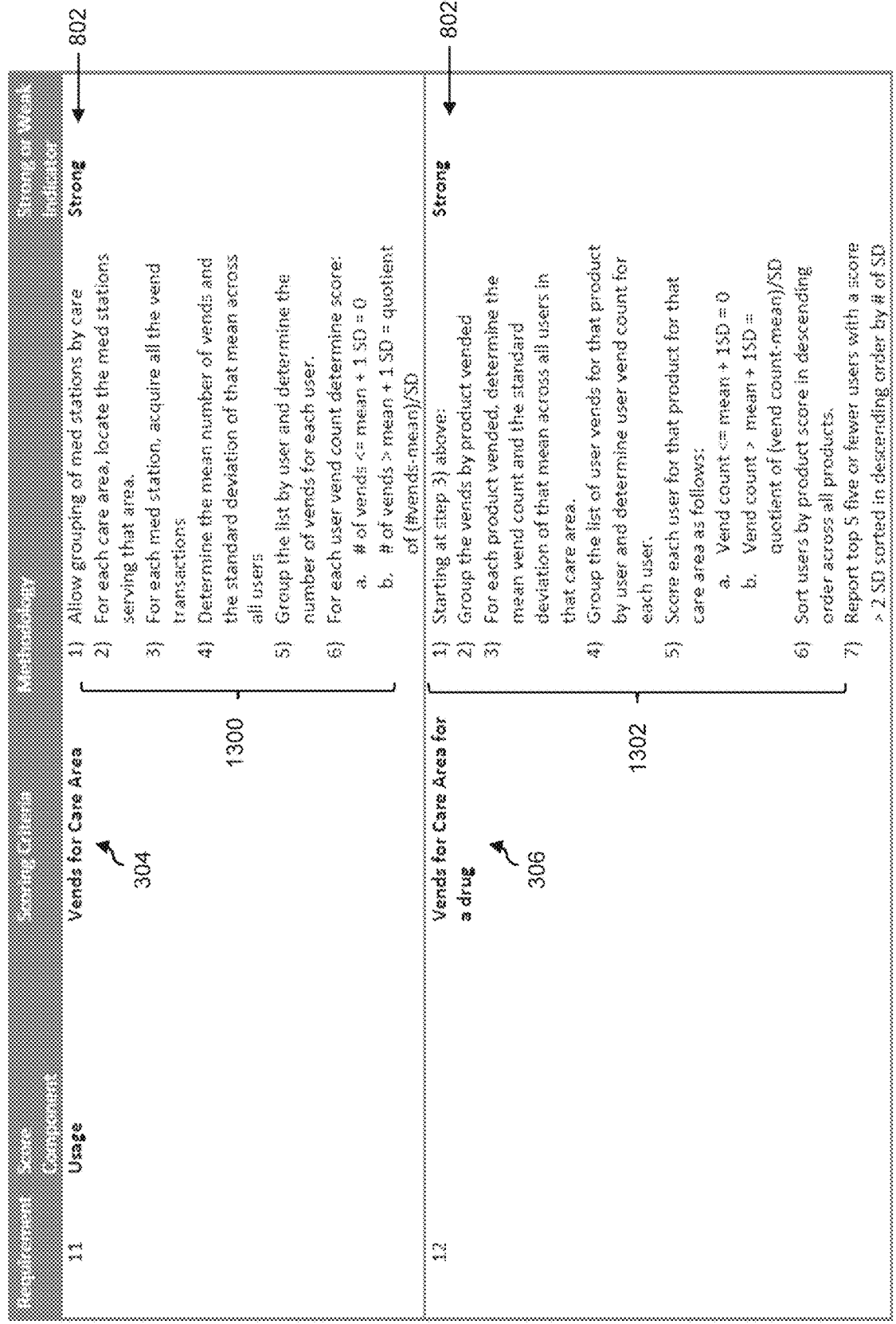
Figure 17:
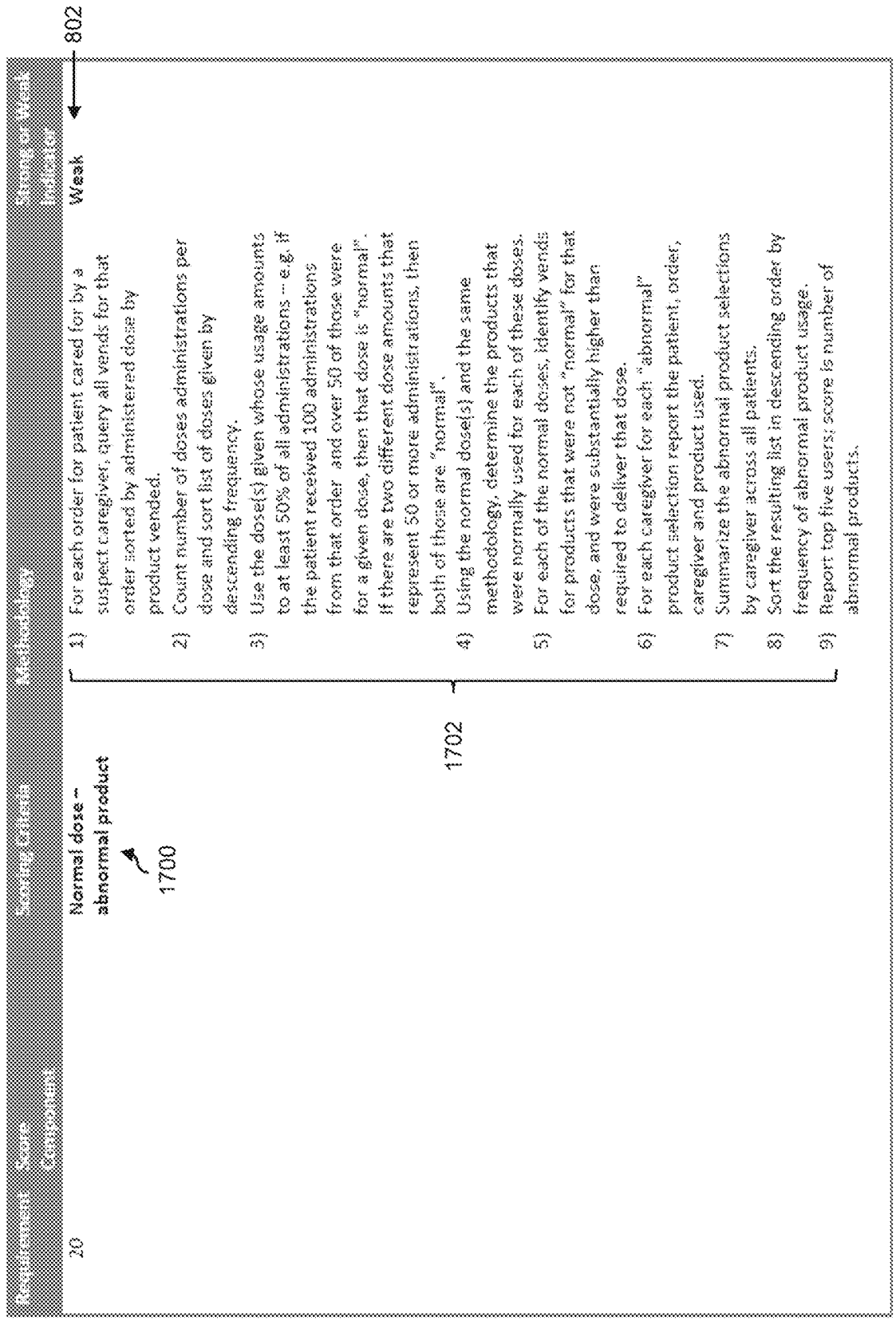
Figure 18:
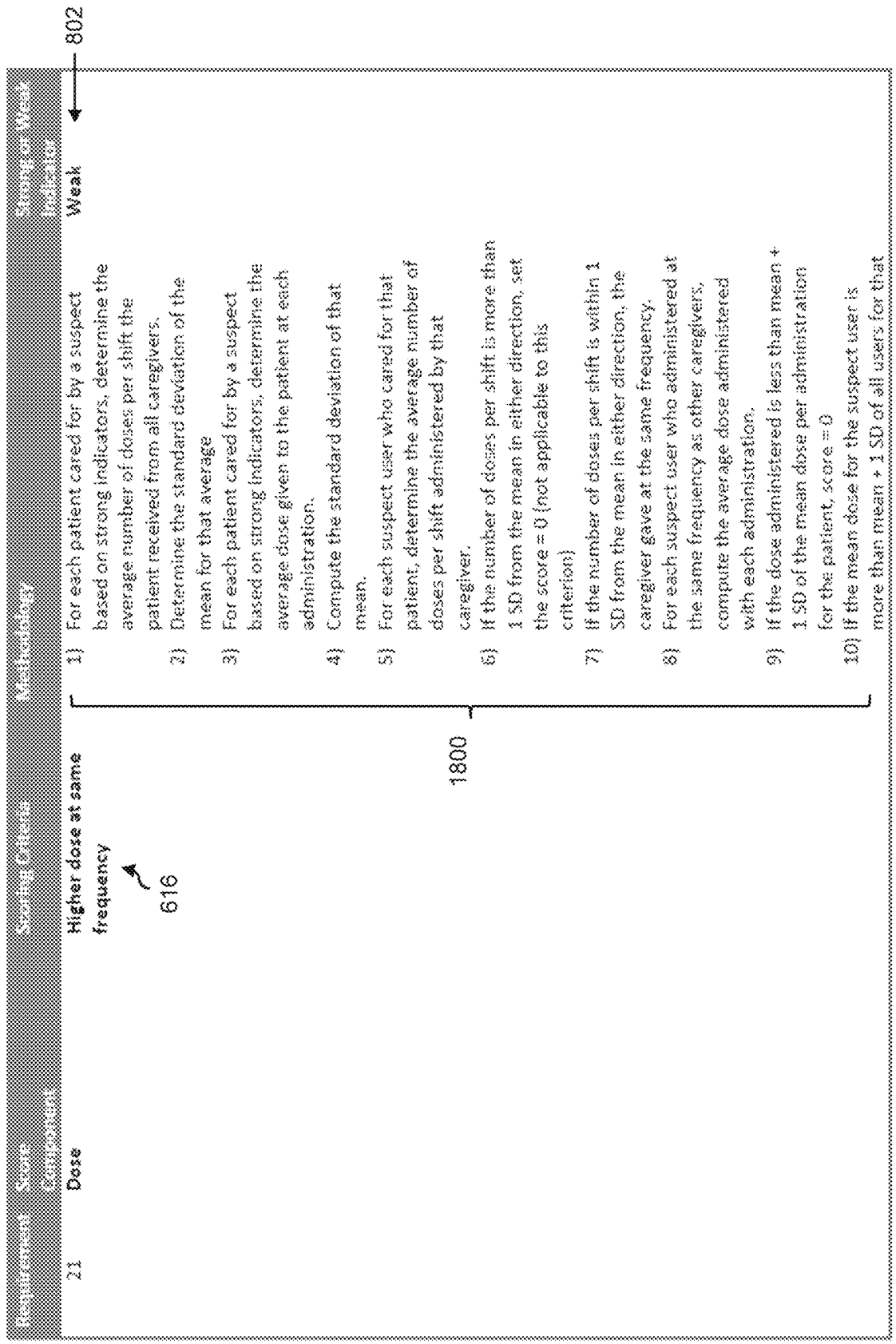

As another example, FIG. 12 shows a process 1200 that may be performed for determining a total usage score 300. Total usage score 300 may be determined using factors in a usage category 1201. In some cases (see, e.g., comment 1206 of FIG. 12), strength 802 may be accompanied by a guidance note related to the factor associated with that strength.

As shown in FIGS. 12-15, factors related to usage category 1201 may be analyzed, such as gross vends 1202, vends for a care area 304, vends of a specific drug for a care area 306, escalating usage over a reporting period for a care area 1400, distributed automatic dispensing cabinet (ADC) usage 310, vend for a discharged patient 312, vend at an ADC that does not normally serve a that patient 314, and removal of outdates 1516. Usage factors 1202, 304, 306, 1400, 310, 312, 314, and 1516 may be determined, respectively using processes 1204, 1300, 1302, 1402, 1404, 1500, 1502, and 1504. Any combination of these usage factors 1202, 304, 306, 1400, 310, 312, 314, and 1516 may be used to provide total usage score 300 using process 1200.

As another example, FIG. 16 shows a process 1600 that may be performed for determining a total dose score 600. Total dose score 600 may be determined using factors in a dose category 1601.

As shown in FIGS. 16-20, factors related to dose category 1601 may be analyzed, such as no administration for the vend 1602, normal dose-abnormal product 1700, higher dose at same frequency 616, doses higher than vended by other caregivers by frequency 614, doses patient less and wastes more 616, withdrawal from multiple ADCs for same patient 602, premature vend 604, vend of oral medication for NPO patient 606, vend of more doses than permitted in the order 608, pain medication given without pain assessment 610, and failure of dose to manage pain 612. Dose factors 1602, 1700, 616, 614, 619, 602, 604, 606, 608, 610, and 612 may be determined, respectively using processes 1604, 1702, 1800, 1900, 1902, 2000, 2002, 2004, 2006, 2008, and 2010. Any combination of these dose factors 1601, 1602, 1700, 616, 614, 619, 602, 604, 606, 608, 610, and 612 may be used to provide total dose score 600 using process 1600.

As another example, FIG. 21 shows a process 2100 that may be performed for determining a total scheduling score 500. Total scheduling score 500 may be determined using factors in a scheduling category 2101.

As shown in FIG. 21, factors related to scheduling category 2101 may be analyzed, such as vends when not on duty 502, vends on evenings and nights 504, occasional staff 508, and weekend vends 506. Scheduling factors 502, 504, 508, and 506 may be determined, respectively using processes 2102, 2104, 2108, and 2106. Any combination of these scheduling factors 502, 504, 508, and 506 may be used to provide total scheduling score 500 using process 2100.

As another example, FIG. 21 shows a process 2110 that may be performed for determining a total discrepancy score 700. Total discrepancy score 700 may be determined using factors in a discrepancy category 2901.

Any of processes 804, 1200, 1600, 2100, and 2110 may be used to determine a value for each of a plurality of health care providers who dispensed controlled medications, wherein each value is associated with a factor that is weighted as a strong factor; to determine which of the plurality of health care providers are potential controlled medication diverters based on the determine values; and to determine at least one of the one or more factor scores for each of the determined potential controlled medication diverters based on additional values associated with factors that are weighted as weak factors.

As shown in FIG. 22, a manual process may require a computer 2200 printing out several types of paper reports 2202 and distributing them to an investigator (e.g., a nurse manager) who must sort through the reports and make guesses as to potential diverters based on their experience and gut instincts. The analysis is all manual and accordingly the investigator may not remember to perform certain steps or may skip steps in the interest of time. As shown in FIG. 22, various operations are performed at a pharmacy 2204, a nursing group or facility 2206, and a risk/loss management facility or group 2208.

FIG. 23 illustrates an automated diversion analytic process according to one or more embodiments. As shown in FIG. 23, one or more computers such as management server 110 may perform a process that includes, at block 2300, assessing strong signal indicators (e.g., factors having a strong strength 812 as discussed herein) associated with categories such as discrepancy, waste, usage, and/or dose variance. At block 2302, computer 110 may build a suspect list (e.g., based on the results of block 2300). At block 2304, computer 110 may assess weak signal indicators (e.g., factors having a weak strength 812 as discussed herein) for each suspect (e.g., potential diverter). At block 2306 computer 110 may compute a diversion score based on the results of blocks 2300 and 2304. At block 2308, computer 110 may rank potential diverters by the total diversion score associated with that potential diverter as determined at block 2306. At block 2310, computer 110 may display and/or print the scoring (e.g., by providing a summary display such as summary display 200 having clickable links to factors, factor scores, categories, monitoring events, or the like as described herein).

In order to facilitate the operations of, for example, block 2300, the system may perform automatic monitoring of dispensing of a controlled medication from a medication dispensing device and may receive (e.g., at management server 110) one or more signals associated with a health care provider who dispensed the controlled medication (e.g., based on the monitoring from the medication dispensing device). The operations of blocks 2300 and 2304 may include determining, by one or more processors, one or more factor scores, where each factor score is associated with one or more of the received signals. The operations of block 2306 may include determining, by one or more processors, a diversion score based on one or more of the determined factor scores. The operations of block 2308 may include determining, by one or more processors, if the health care provider is a potential controlled medication diverter based on the diversion score.

For example, a system such as system 100 may help ensure that no steps are skipped or forgotten. The system may also display or print the result of this more-extensive scoring and the pharmacy portion 2312 of the system may perform various operations as shown in FIG. 23 such as providing or printing out a dossier that contains the details of all the scoring that the investigator would otherwise have to assemble, for example. FIG. 23 also shows various operations that may be facilitated and performed at a nursing group or facility 2314, and a risk/loss management facility or group 2316. Thus, the investigator's only responsibility may be to look at certain weak factors the system may not be set up to detect (e.g., absenteeism, performance problems, and the like). Accordingly, the diversion analytic forensic process may occur much more quickly and completely, while utilizing a volume of factors that is essentially impossible or cost prohibitive to do manually.

Many of the examples described above include factor score computations based on a number of standard deviations from the mean. However, it should be appreciated that this is merely illustrative and other statistical measures and/or methods (e.g., advanced analytics methods) can be applied to identify factor scores that are outliers, to identify additional factors to be scored, and/or to identify cross-factor scores and associated cross-factor score outliers. For example, adaptive statistical analysis may be provided that dynamically identifies factors and factor score outliers to allow detection methods to evolve as the diverter population adapts its own behavior to controls being put into place.

For example, advanced analytics of transactional data from an automated dispensing system (e.g., Pyxis-ES' automated dispensing system) and from other, external systems (e.g., electronic medical records, caregiver scheduling systems, and caregiver time-and-attendance systems) may be applied to statistically determine the probability that a particular user's performance may indicate drug diversion. Specifically, the advanced analytics may be applied to evaluate a population of transactions regarding specific classes of medications. Advanced analytics may also be applied to 1) normalize usage across users to account for differences in duration of work during the analysis period, 2) compute normalized statistical behavior around a transactional user role (e.g., a role for a nurse, pharmacist, pharmacy technician, anesthesiologist, CRNA, etc.). 3) compute performance against categories of known "strong" indicators of diversion including, but not limited to a) Usage, b) Cancellation, c) Waste of partial or total medication doses, and/or d) Discrepancy management as described herein, 4) for each category, compute statistical behavior around specific sub categories (e.g., for waste behavior, computing statistical behavior for a duration of time between dispensing and waste of an unused portion, tendency to waste at a device other than the device from which it was vended, proportion of undocumented waste, and/or the like), 5) for each category, compute sub-category-specific statistical analytics to derive the nature of outliers for that population, 6) for each category, compute relationships between the sub-categories that describe strong associations (e.g., either positive or negative associations) between subcategories (e.g., to determine a strong positive relationship between the tendency for long duration between dispense and waste with a tendency to waste at a med station other than the one from which the dose was dispensed), and/or 7) provide summary information on strong indicators showing outliers in each subcategory described using statistical and graphic plots to identify individuals who are strong outliers in one or more subcategory of each strong indicator.

The systems and methods described herein may be flexible for identifying potential drug diverters to handle a continuing change in the diversion of medications. In the acute care setting, diversion exists primarily to fuel personal addictions. Such addictions drive healthcare providers to become very creative in masquerading their diversion as ordinary use in healthcare delivery. Because the addictive compulsion is so strong, addicts become very creative in finding ways to continue to divert to supply their habits. As a result, the methods described herein are adaptive to continue to be effective even as the diverter population adapts its own behavior to controls being put into place.

The systems and methods described herein may provide several advantages over current known methods. For example, current methods look solely at transactions around controlled substances. While these are the most likely to be diverted, diversions of medications that are not controlled substances, and that can be used as surrogates or to potentiate the effects of controlled substances, can also be tracked to serve as diversion indicators. As opposed to current methods, this method can be aimed at any particular population of medications.

As another example, current methods rely on very coarse indicators of aberrant behavior determined by gross usage and cancellation behavior. In contrast, the systems and methods described herein measure and track much more discrete behavioral metrics. For example, where current methods measure waste, the systems and methods described herein measure and track multiple specific behaviors around waste.

In some situations, methods may be provided in which the healthcare facility empirically establishes thresholds (e.g., in the form of a number of standard deviations of the mean). However, in some implementations, advanced analytics may be used to analyze population statistics to permit the data itself to establish what outlier thresholds should be. Moreover, those threshold computations may be applied to the more discrete behavioral subcategories described herein. Further, the systems and methods described herein may continually re-define the definition of outlier performance based on changes in the data.

As another example, current methods rely on user review of various reports to draw associations between behaviors. The systems and methods described herein may provide an automatic association that applies reliable statistical methods to the determination beyond the capabilities of a human investigator.

As another example, current methods are static and are sensitive to only a small subset of the forensic evidence. In contrast, the systems and methods disclosed herein are dynamic. For example, the statistical methods described herein can be applied to any behavior that is measurable from available data.

As another example, current methods are capable of defining only known diversion behaviors. In contrast, the systems and methods described herein may permit ongoing statistical analysis to define new patterns of diversion behavior.

In some examples described herein, factor score and/or diversion score outliers may be identified based on computation of standard deviations of mean usage behavior with user assigned thresholds, typically at 2-3 standard deviations above the mean, and may be aimed primarily at the nurse/caregiver population for a particular patient population. However, advanced analytics may be applied to permit the data to dynamically determine the definition of outlier behavior based on a user role and a patient population (e.g., populations ranging from patients served on a particular cabinet to all patients in a given hospital). In various implementations, applying advanced analytics may include computing a "z-score", for each user in a role, that normalizes that user's activity rate against the number of transactions they have in the data the invention reviews. As a result, users who work longer hours do not stand out over users who work fewer hours. In various implementations, applying advanced analytics may include applying statistical techniques such as box-plot demonstrations of outlier behavior that cause significant outliers to be visually identifiable.

Although various examples have been described herein in the context of diversion detection in a hospital or integrated delivery network, it should be appreciated that the systems and methods described herein can be applied to identify diverters on a larger scale such as a citywide scale, a statewide scale, a national scale, or a worldwide scale. For example, nationally stored controlled substances transaction data and customer reports of diversion can be used to develop and maintain a national registry of caregivers known or suspected to have diverted controlled substances.

Diversion of controlled substances is a national, endemic problem with significant public health consequences. Recent reports (2015, 2016) have highlighted cases where caregivers had become addicts, diverted injectable narcotics and replaced them with surrogates (usually saline injection) contaminated with their blood, resulting in many patients being exposed to and actually contracting HIV and Hepatitis.

Diversion is generally a crime of opportunity, and exists within hospitals because there are caregivers (e.g., primarily nurses, anesthesiologists, and pharmacy personnel) who have legitimate access to controlled substances in the course of their normal practice. Nationally prominent reports have also included surgical technicians and radiology technicians as diverters.

Diverters exploit this access typically by finding ways to mask their activities in the guise of obtaining medication as ordered for patient use. For example, the user may initiate a dispense transaction and then cancel it after having removed medication for themselves, or may withdraw the maximum ordered dose of a pain medication for a patient, when the patient needs none, or needs less than what they took out. Because this drug-seeking behavior is compulsive, there are patterns of this masking behavior that become evident over time in dispensing transactions.

Hospitals have traditionally shied away from identifying or prosecuting these addicted caregivers. Some hospitals send these caregivers to rehabilitation, and then turn them loose into the workforce. In many cases, these addicts simply move on to jobs at other hospitals, often in different parts of the same state or in different states. Even if action is taken, licensure often occurs on a state-by-state basis and so an employer has no appropriate way to know whether or not the addict has a history of diversion until or unless they are caught and prosecuted.

These "travelers" become adept at "flying under the radar" within a hospital system and detecting when their activities are drawing attention, and simply move to another location. Typically they get caught when their drug-seeking behavior overrides their caution. Thus it is likely that there are addicts currently working who have simply never stayed at any location long enough to get caught.

The systems and methods described herein can include a national repository of medication dispensing transactions in the cloud. As part of this repository, the system may keep track of every individual user across an area (e.g., across the US marketplace) and the medication dispensing transactions performed by each user. This information can be used to identify potential diverters by analyzing these transactions for exceptional usage of controlled substances as previously described.

In various implementations, a nationally unique identifier (e.g., Social Security Number) may be captured as part of a user credentialing process. The system (e.g., server 110) may maintain transaction, dispensing, and/or other information in a national registry of users according to the unique identifier. The system may then use this identifier to identify potential diverters at different sites within the area as being the same individual based on the identifier.

The system may maintain a timeline of the interaction between the caregiver (e.g., as identified by the nationally unique identifier) and the dispensing system at various sites in a registry. The system may compare the frequency of location change for any system user to national and regional averages, and identify outliers as 'travelers'.

The diversion analytics portion of the system may then use the identification of a user as a 'traveler' to augment its scoring of users as potential diverters. Scoring of a user at any particular site may also cause a stored history for that user to be annotated with suspicion of diversion. The system may provide a mechanism within the diversion analytics system by which an authorized user of the system could either upgrade that notation to that of a known diverter, or could indicate that the user was cleared of suspicion.

System users could then inquire of this registry during the hire process to determine if a caregiver they intend to hire has had frequent job changes, with or without suspicion of or dismissal for drug diversion.

A national application of the diversion monitoring systems and methods discussed herein may extend the analytics, from specific individual sites based on indications of excessive usage of controlled substances, to be able to recognize that a caregiver has unusually frequent job and location changes, and, if appropriate, that they had been previously suspected of being a diverter. This would permit diversion analytics to trace behavior across a wider swath of geography and time.

The systems and methods described herein may provide solutions to problems in the prior art by creating a national registry of users of medication dispensing systems using a nationally unique identifier to identify when user records at various sites represent the same individual (e.g., since all transactions from a dispensing systems may be date and/or time stamped with the user identity as known at that site and stored in a single national database in the cloud). In such a system, capturing this information would be facilitated by the applications capturing the user information also capturing this nationally unique identifier.

This analytics data store may be used to create a registry of users and their appearance at various sites across the nation, as well as notations regarding whether or not they had been suspected of diversion, or had been identified as known diverters. Healthcare facilities could then inquire of this registry and determine if a potential hire had a suspicious job history, especially if that history involved suspicion of or dismissal for drug diversion.

A diversion analytics engine associated with a store such as a cloud store of analytics data may be augmented to use apparent 'travelers' as additional scoring inputs when attempting to locate caregivers suspected of diversion.

For example, 1) dispensing and infusion technologies may be augmented to capture a nationally unique identifier, such as a social security number, for each credentialed user, 2) the cloud transaction storage system may capture the identifier and associate it with all known user definitions using the same nationally unique identifier. 3) this would create a registry (e.g., within the cloud) that would maintain a timeline for each time a user with the nationally unique identifier interacted with any dispensing or infusion device, 4) the diversion analytics function associated with these registries may monitor the registries for indications that a given nationally unique identifier is associated with frequent customer and/or location changes using proprietary algorithms, and may mark such individuals as travelers, 5) the diversion analytics functions may analyze usage of controlled substances for evidence of possible diversion, which may be augmented to recognize a user as a 'traveler' as part of its scoring system, 6) if the diversion analytics system at any particular site were to identify a user as being suspected of diversion, the system may create an annotation in the timeline associated with the user's nationally unique identifier, 7) if the suspect became known as a diverter, that notation would be added to the timeline associated with that user's nationally unique identifier, 8) if the suspect was dismissed under suspicion of diversion, that notation may be added to the timeline, 9) if the suspect were cleared of suspicion after being flagged as a suspect, that notation may be added to the timeline associated with the user's nationally unique identifier, 10) if a customer were concerned about a particular employee, the system may provide a portal by which an authorized user could inquire about their history on the system (e.g., the system may include an opt-in system by which each site may identify what information would be available to other users on this portal and/or the portal may accept the user's user identification at the inquiring customer site, and return a timeline showing date/time, city and state, and any annotations of suspicion, clearing, dismissal or known diversion), 11) the system may include a mechanism by which an authorized employer could query a specific nationally unique identifier directly and receive the timeline.

In various implementations the system may include a completely external and separate database for the repository. In various implementations the system may include a database that contains only the SSN and the indication of suspect or known diverter. In this case, inquiry by an investigator may result in delivery only the history of location(s) at which the user had worked and any indication of their being a suspected or known diverter.

In various implementations the system may return the name of the site and/or name of the individual facility (e.g., where a site manager has several sites) if the site manager opted to make that information available.

The systems and methods discussed herein may include and be facilitated by a national capture of all users of a widely disseminated dispensing system currently used by pharmacists, nurses and anesthesiologists. The Social Security Number is a nationally managed and generally reliable national unique personal identifier. The use of this identifier would require careful control to prevent identity theft or inappropriate alteration. System databases that store information associated with social security numbers may be designed for this purpose and to ensure security of protected healthcare information (ePHI) as described under the HIPAA and HITECH acts and their related federal regulations.

In various implementations, systems and methods are provided for detecting 'travelers' and using that information to compute the likelihood of a user being a diverter are part of this invention. Travelers are known to be individuals who change locations frequently within the same site, as well as changing locations to different facilities and facilities in different cities and states. The systems and methods described herein use statistical analysis to identify what kinds of changes (e.g., both in frequency and distance) are normal and identifies outliers (e.g., location changes that are more frequent and occur over longer distances) as 'travelers'. Identification of a user being a 'traveler' is one of several indicators that a user may be a diverter. Such identification may become one more inputs into a larger computation of likelihood of being a diverter using, for example, the methods described above in connection with FIGS. 8-21 and 23.

Figure 24:
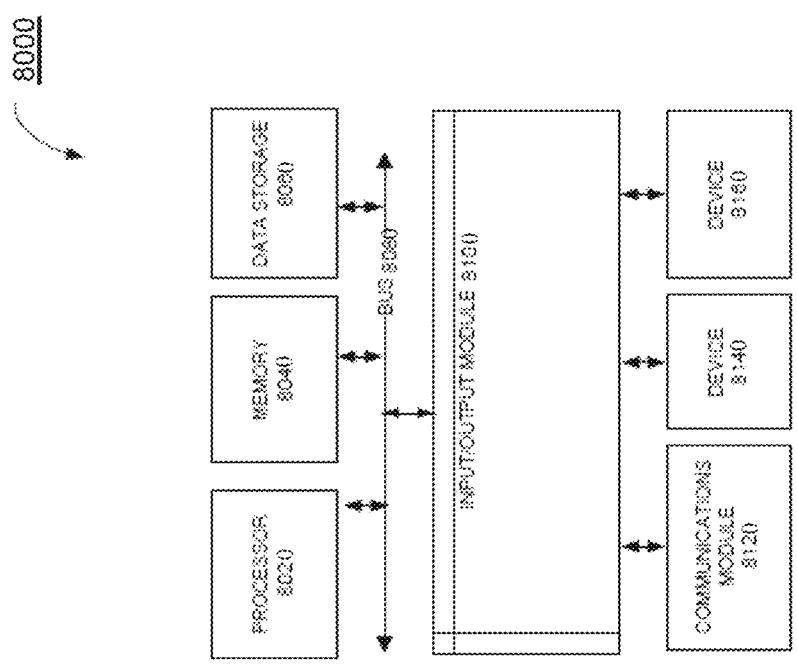
FIG. 24 conceptually illustrates an electronic system with which one or more aspects of the subject technology may be implemented.

FIG. 24 conceptually illustrates electronic system 8000 with which one or more embodiments of the subject technology may be implemented. Electronic system 8000, for example, can be a medication dispensing device 140, a waste device 150, a server 110, 120, a desktop computer, a laptop computer, a tablet computer, a phone, a personal digital assistant (PDA), or generally any electronic device that transmits signals over a network (e.g., time clocks, proximity badges, biometric identification schemes, and the like). Such an electronic system includes various types of computer readable media and interfaces for various other types of computer readable media. Electronic system 8000 includes bus 8080, processing unit(s) 8120, system memory 8040, read-only memory (ROM) 8100, permanent storage device 8020, input device interface 8140, output device interface 8060, and network interface 8160, or subsets and variations thereof.

Bus 8080 collectively represents all system, peripheral, and chipset buses that communicatively connect the numerous internal devices of electronic system 8000. In one or more embodiments, bus 8080 communicatively connects processing unit(s) 8120 with ROM 8100, system memory 8040, and permanent storage device 8020. From these various memory units, processing unit(s) 8120 retrieves instructions to execute and data to process in order to execute the processes of the subject disclosure. The processing unit(s) can be a single processor or a multi-core processor in different embodiments.

ROM 8100 stores static data and instructions that are needed by processing unit(s) 812 and other modules of the electronic system. Permanent storage device 8020, on the other hand, is a read-and-write memory device. This device is a non-volatile memory unit that stores instructions and data even when electronic system 8000 is off. One or more embodiments of the subject disclosure use a mass-storage device (such as a magnetic or optical disk and its corresponding disk drive) as permanent storage device 8020.

Other embodiments use a removable storage device (such as a floppy disk, flash drive, and its corresponding disk drive) as permanent storage device 8020. Like permanent storage device 8020, system memory 8040 is a read-and-write memory device. However, unlike storage device 8020, system memory 8040 is a volatile read-and-write memory, such as random access memory. System memory 8040 stores any of the instructions and data that processing unit(s) 8120 needs at runtime. In one or more embodiments, the processes of the subject disclosure are stored in system memory 8040, permanent storage device 8020, and/or ROM 8100. From these various memory units, processing unit(s) 8120 retrieves instructions to execute and data to process in order to execute the processes of one or more embodiments.

Bus 8080 also connects to input and output device interfaces 8140 and 8060. Input device interface 8140 enables a user to communicate information and select commands to the electronic system. Input devices used with input device interface 8140 include, for example, alphanumeric keyboards and pointing devices (also called "cursor control devices"). Output device interface 8060 enables, for example, the display of images generated by electronic system 8000. Output devices used with output device interface 806 include, for example, printers and display devices, such as a liquid crystal display (LCD), a light emitting diode (LED) display, an organic light emitting diode (OLED) display, a flexible display, a flat panel display, a solid state display, a projector, or any other device for outputting information. One or more embodiments may include devices that function as both input and output devices, such as a touchscreen. In these embodiments, feedback provided to the user can be any form of sensory feedback, such as visual feedback, auditory feedback, or tactile feedback; and input from the user can be received in any form, including acoustic, speech, or tactile input.

Also as shown in FIG. 24, bus 8080 also couples electronic system 8000 to a network (not shown) through network interface 8160. In this manner, the computer can be a part of a network of computers (such as a local area network ("LAN"), a wide area network ("WAN"), or an Intranet, or a network of networks, such as the Internet. Any or all components of electronic system 8000 can be used in conjunction with the subject disclosure.

Many of the above-described features and applications may be implemented as software processes that are specified as a set of instructions recorded on a computer readable storage medium (alternatively referred to as computer-readable media, machine-readable media, or machine-readable storage media). When these instructions are executed by one or more processing unit(s) (e.g., one or more processors, cores of processors, or other processing units), they cause the processing unit(s) to perform the actions indicated in the instructions. Examples of computer readable media include, but are not limited to, RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, ultra density optical discs, any other optical or magnetic media, and floppy disks. In one or more embodiments, the computer readable media does not include carrier waves and electronic signals passing wirelessly or over wired connections, or any other ephemeral signals. For example, the computer readable media may be entirely restricted to tangible, physical objects that store information in a form that is readable by a computer. In one or more embodiments, the computer readable media is non-transitory computer readable media, computer readable storage media, or non-transitory computer readable storage media.

In one or more embodiments, a computer program product (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

While the above discussion primarily refers to microprocessor or multi-core processors that execute software, one or more embodiments are performed by one or more integrated circuits, such as application specific integrated circuits (ASICs) or field programmable gate arrays (FPGAs). In one or more embodiments, such integrated circuits execute instructions that are stored on the circuit itself.

The subject technology is illustrated, for example, according to various aspects described above. Various examples of these aspects are described as numbered concepts or clauses (1, 2, 3, etc.) for convenience. These concepts or clauses are provided as examples and do not limit the subject technology. It is noted that any of the dependent concepts may be combined in any combination with each other or one or more other independent concepts, to form an independent concept. The following is a non-limiting summary of some concepts presented herein:

Concept 1. A method for identifying a potential controlled medication diverter, the method comprising:
automatically monitoring dispensing of a controlled medication from a medication dispensing device;
receiving one or more signals associated with a health care provider who dispensed the controlled medication;
determining, by one or more processors, one or more factor scores, wherein each factor score is associated with one or more of the received signals;
determining, by one or more processors, a diversion score based on one or more of the determined factor scores; and
determining, by one or more processors, if the health care provider is a potential controlled medication diverter based on the diversion score.

Concept 2. The method of Concept 1 or any other Concept, further comprising:
determining a weighted ranking of each factor score; and
wherein the determining the diversion score is further based on the determined weighted rankings of the factor scores.

Concept 3. The method of Concept 1 or any other Concept, further comprising:
providing a notification to an authorized user if the health care provider is determined to be a potential controlled medication diverter.

Concept 4. The method of Concept 1 or any other Concept, further comprising:
determining a diversion score for each of a plurality of health care providers who dispensed controlled medications; and
providing a ranked listing of a group of the plurality of health care providers based on the diversion scores.

Concept 5. The method of Concept 4 or any other Concept, further comprising:
providing a listing of one or more of the diversion scores and one or more of the factor scores associated with each listed health care provider.

Concept 6. The method of Concept 5 or any other Concept, further comprising:
determining a weighted ranking of each factor score and each diversion score; and
providing a visual indication of the weighted rankings of each listed score.

Concept 7. The method of Concept 1 or any other Concept, wherein one factor score is a total waste score based on one or more factors comprising (i) more waste than normal; (ii) unverified waste; (iii) long delays between vend and waste; (iv) waste of whole doses; (v) vend and waste performed at different med stations; (vi) waste doses with another potential abuser; and (vii) vends of higher dose product that generate higher waste when exact or smaller doses are available.

Concept 8. The method of Concept 1 or any other Concept, wherein one factor score is a total usage score based on one or more factors comprising (i) gross vends; (ii) vends for a care area; (iii) vends of a specific drug for a care area; (iv) escalating usage over a reporting period for a care area; (v) distributed automatic dispensing cabinet (ADC) usage; (vi) vend for a discharged patient; (vii) vend at an ADC that does not normally serve a that patient; and (viii) removal of outdates.

Concept 9. The method of Concept 1 or any other Concept, wherein one factor score is a total dose score based on one or more factors comprising (i) no administration for the vend; (ii) normal dose-abnormal product; (iii) higher dose at same frequency; (iv) doses higher than vended by other caregivers by frequency; (v) doses patient less and wastes more; (vi) withdrawal from multiple automatic dispensing cabinets (ADCs) for same patient; (vii) premature vend; (viii) vend of oral medication for a nothing by mouth (NPO) patient; (ix) vend of more doses than permitted in the order; (x) pain medication given without pain assessment; and (xi) failure of dose to manage pain.

Concept 10. The method of Concept 1 or any other Concept, wherein one factor score is a total scheduling score based on one or more factors comprising (i) vends when not on duty; (ii) vends on evenings and nights; (iii) occasional staff; and (iv) weekend vends.

Concept 11. The method of Concept 1 or any other Concept, wherein one factor score is a total hardware score based on one or more factors comprising unexpected opens from medical dispensing devices.

Concept 12. The method of Concept 1 or any other Concept, wherein one factor score is a total discrepancy score based on one or more factors comprising:

discrepancy incidence on unit;
discrepancy across incidence across units; and
discrepancy by drug.

Concept 13. A non-transitory machine-readable medium embodying instructions that, when executed by a machine, cause the machine to perform a method for identifying a potential controlled medication diverter, the method comprising:
automatically date stamping, time stamping, or user stamping, by a medication dispensing device, each dispensing transaction performed at the medication dispensing device;
receiving one or more signals associated with a health care provider who dispensed the controlled medication;
determining one or more factor scores, wherein each factor score is associated with one or more of the received signals;
determining a diversion score based on one or more of the determined factor scores; and
determining if the health care provider is a potential controlled medication diverter based on the diversion score.

Concept 14. The non-transitory machine-readable medium of Concept 13 or any other Concept, wherein the method further comprises:
determining a weighted ranking of each factor score, wherein the determining the diversion score is further based on the determined weighted rankings of the factor scores; and
providing a notification to an authorized user if the health care provider is determined to be a potential controlled medication diverter.

Concept 15. The non-transitory machine-readable medium of Concept 13 or any other Concept, wherein the method further comprises:
determining a diversion score for each of a plurality of health care providers who dispensed controlled medications; and
providing a ranked listing of a group of the plurality of health care providers based on the diversion scores.

Concept 16. The non-transitory machine-readable medium of Concept 15 or any other Concept, wherein the method further comprises:
providing a listing of one or more of the diversion score and one or more of the factor scores associated with each listed health care provider;
determining a weighted ranking of each factor score and each diversion score; and
providing a visual indication of the weighted rankings of each listed score.

Concept 17. The non-transitory machine-readable medium of Concept 13 or any other Concept, wherein the determining the one or more factor scores further comprises:
determining a value for each of a plurality of health care providers who dispensed controlled medications, wherein each value is associated with a factor that is weighted as a strong factor;
determining which of the plurality of health care providers are potential controlled medication diverters based on the determine values; and
determining at least one of the one or more factor scores for each of the determined potential controlled medication diverters based on additional values associated with factors that are weighted as weak factors.

Concept 18. A system for identifying potential controlled medication diverters, the system comprising:
one or more automated dispensing cabinets;
one or more processors; and
a memory including instructions that, when executed by the one or more processors, cause the one or more processors to:
automatically monitor dispensing of controlled medications from the one or more automated dispensing cabinets;
receive signals associated with each health care provider who dispenses controlled medications from the one or more automated dispensing cabinets;
determine a factor score for each of the received signals;
determine a diversion score based on one or more of the determined factor scores; and
determine which of the health care providers are potential controlled medication diverters based on the determined diversion scores.

Concept 19. The system of Concept 18 or any other Concept, wherein the instructions, when executed by the one or more processors, further cause the one or more processors to:
display a list of the determined potential controlled medication diverters with the diversion score and one or more of the factor scores associated with each potential controlled medication diverter.

Concept 20. The system of Concept 19 or any other Concept, wherein the instructions, when executed by the one or more processors, further cause the one or more processors to:
determine a weighted ranking of each factor score and each diversion score; and
provide a visual indication of the weighted ranking of each diversion and factor score displayed on the list.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that any specific order or hierarchy of blocks in the processes disclosed is an illustration of example approaches. Based upon design preferences, it is understood that the specific order or hierarchy of blocks in the processes may be rearranged, or that all illustrated blocks be performed. Any of the blocks may be performed simultaneously. In one or more embodiments, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The predicate words "configured to", "operable to", and "programmed to" do not imply any particular tangible or intangible modification of a subject, but, rather, are intended to be used interchangeably. In one or more embodiments, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as an "aspect" may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as a "configuration" may refer to one or more configurations and vice versa.

The word "exemplary" is used herein to mean "serving as an example, instance, or illustration." Any embodiment described herein as "exemplary" or as an "example" is not necessarily to be construed as preferred or advantageous over other embodiments. Furthermore, to the extent that the term "include," "have," or the like is used in the description or the claims, such term is intended to be inclusive in a manner similar to the term "comprise" as "comprise" is interpreted when employed as a transitional word in a claim. Furthermore, to the extent that the term "include," "have," or the like is used in the description or the claims, such term is intended to be inclusive in a manner similar to the term "comprise" as "comprise" is interpreted when employed as a transitional word in a claim.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

Reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject disclosure.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The subject matter of this specification has been described in terms of particular aspects, but other aspects can be implemented and are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other variations are within the scope of the following claims.

What is claimed is:

1. A method for identifying a controlled medication diverter, comprising:
   providing a plurality of dispensing devices configured to automatically monitor dispensing of a controlled medication from the dispensing devices;
   configuring each dispensing device to automatically, based on receiving an authorization credential at the dispensing device, capture and associate a time and a user identity of a respective user performing a dispensing transaction at the dispensing device;
   automatically monitoring, by a plurality of dispensing devices, dispensing of controlled medication from the dispensing devices;
   by each dispensing device, automatically capturing and associating the time and the user identity of each user performing a dispensing transaction at the dispensing device;

receiving, from the dispensing devices, based on respective user identities captured at the dispensing devices, one or more signals associated with each medication that was dispensed from the dispensing devices and the respective user who dispensed the medication;

identifying, by one or more processors, a plurality of user activities performed by a plurality of users in connection at least one medication and a plurality of devices, the plurality of devices including the plurality of dispensing devices;

determining, by the one or more processors, first factor scores for the plurality of users based on the plurality of user activities, wherein the first factor scores comprise a score for waste activities and a usage score associated with an amount of medication usage;

generating, by the one or more processors, respective first diversion scores for the plurality of users based on an evaluation of the identified plurality of user activities and the first factor scores across caregivers associated with a patient population;

identifying, by the one or more processors, from the plurality of users, a plurality of suspected diverters based on the respective first diversion scores for the plurality of users;

after generating the respective first diversion scores and identifying the plurality of suspected diverters based on the respective first diversion scores, for each identified diverter of the plurality of suspected diverters:
automatically determining, by the one or more processors, one or more second factor scores for the identified diverter based on patient records for patients being cared for by the identified diverter or based on caregiver scheduling data associated with the identified diverter;
generating and storing, by the one or more processors, respective total diversion scores for the plurality of suspected diverters based on the first diversion scores for the suspected diverters and the second factor scores determined after identifying the plurality of suspected diverters; and
automatically selecting, by the one or more processors, based on the respective total diversion scores and the one or more second factor scores, a plurality of selected diverter suspects from the suspected diverters; and
generating a user interface that identifies the selected diverter suspects, together with, for each selected diverter suspect, a series of graphic indicators representative of the respective activities contributing to the total diversion score associated with the selected diverter suspect, wherein the user interface is configured to, when a user selects a respective graphical indicator of the series of graphic indicators, display dispensing transactions performed at one or more of the plurality of dispensing devices by the selected diverter suspect associated with the respective graphical indicator.

2. The method of claim 1, wherein a user activity of the plurality of user activities comprises a device usage associated with a single user across a plurality of distributed dispensing devices; and
wherein determining a first diversion score for the single user comprises comparing the device usage with device usages of other users associated with the patient population.

3. The method of claim 1, wherein a user activity of the plurality of user activities comprises a waste activity;
wherein the plurality of devices comprises a waste device; and
wherein determining a first diversion score of a first user of the plurality of users comprises comparing a waste amount of the first user with waste amounts of other users associated with the patient population.

4. The method of claim 1, wherein at least one factor score of the first factor scores comprises a waste score based on the user being associated with one or more of: (i) more waste than normal; (ii) unverified waste; (iii) long delays between vend and waste; (iv) waste of whole doses; (v) vend and waste performed at different med stations; (vi) waste doses with another potential abuser; and (vii) vends of higher dose product that generate higher waste when exact or smaller doses are available.

5. The method of claim 1, wherein a user activity of the plurality of user activities comprises a first user of the plurality of users dispensing a dosage of a respective medication from a dispensing device; and
wherein determining a first diversion score of the first user comprises determining that the dosage dispensed from the dispensing device by the first user is a higher dosed product than a dosage dispensed by other users for the same patient.

6. The method of claim 1,
wherein at least one factor score of the first factor scores comprises a score based on the user being associated with one or more of: (i) gross vends that are in a higher amount than other users in a same role as the user; (ii) vends for a care area that are in a higher amount than other users in the care area; (iii) vends of a specific drug for a care area that are in a higher amount than other users in the care area; (iv) escalating usage over a reporting period for a care area; (vi) a vend for a discharged patient; (vii) a vend at an ADC that does not normally serve a patient associated with the vend; (viii) no administration for a vend; (ix) doses higher than vended by other caregivers by frequency; (x) withdrawal from multiple automatic dispensing cabinets (ADCs) for same patient; (xi) premature vend; (xii) vend of oral medication for a nothing by mouth (NPO) patient; (xiii) vend of more doses than provided in an order; (xiv) a vend of pain medication for a patient without a pain assessment; and (xv) a vend when the user is not on duty.

7. The method of claim 1, further comprising:
determining a weighted ranking of each first and second factor score; and
wherein the determining the first diversion scores is further based on the determined weighted rankings of the first and second factor scores.

8. The method of claim 1, further comprising:
providing a notification to an authorized user responsive to determining a first user of the plurality of users is a suspected diverter.

9. A non-transitory machine-readable medium embodying instructions that, when executed by a machine, cause the machine to perform operations, comprising:
configuring a plurality of dispensing devices to automatically monitor dispensing of a controlled medication from the plurality of dispensing devices;
monitoring the dispensing of the controlled medication from the plurality of dispensing devices, wherein each dispensing device is configured to automatically, based on receiving an authorization credential at the dispensing device, capture and associate a time and a user identify of a respective user performing a dispensing transaction at the dispensing device; receiving, from each dispensing device, based on respective user identities captured at the dispensing device, one or more signals associated with each medication that was dispensed from the dispensing device and the respective user who dispensed the medication from the dispensing device;

identifying, by one or more processors, a plurality of user activities performed by a plurality of users in connection at least one medication and a plurality of devices, the plurality of devices including the plurality of dispensing devices;

determining first factor scores for the plurality of users based on the plurality of user activities, wherein the first factor scores comprise a score for waste activities and a usage score associated with an amount of medication usage;

generating respective first diversion scores for the plurality of users based on an evaluation of the identified plurality of user activities and the first factor scores across caregivers associated with a patient population;

identifying, by the one or more processors, from the plurality of users, a plurality of suspected diverters based on the generated first diversion scores for the plurality of users;

after generating the respective diversion scores and identifying the plurality of suspected diverters based on the respective diversion scores, for each identified diverter of the plurality of suspected diverters:

automatically determining one or more second factor scores for the identified diverter based on patient records for patients being cared for by the identified diverter or based on caregiver scheduling data associated with the identified diverter;

generating and storing, by the one or more processors, respective total diversion scores for the plurality of suspected diverters based on the first diversion scores and the second factor scores determined after identifying the plurality of suspected diverters; and automatically selecting, by the one or more processors, based on the respective total diversion scores and the one or more second factor scores, a plurality of selected diverter suspects, from the suspected diverters; and generating a user interface that identifies the selected diverter suspects, together with, for each selected diverter suspect, a series of graphic indicators representative of the respective activities contributing to the total diversion score associated with the selected diverter suspect, wherein the user interface is configured to, when a user selects a respective graphical indicator of the series of graphic indicators, display dispensing transactions performed at one or more of the plurality of dispensing devices by the selected diverter suspect associated with the respective graphical indicator.

10. The non-transitory machine-readable medium of claim 9, wherein a user activity of the plurality of user activities comprises a device usage associated with a single user across a plurality of distributed dispensing devices; and wherein determining a first diversion score for the single user comprises comparing the device usage with device usages of other users associated with the patient population.

11. The non-transitory machine-readable medium of claim 9, wherein the plurality of devices comprises a waste device, wherein at least one factor score of the first factor scores comprises a waste score based on the user being associated with one or more of: (i) more waste than normal; (ii) unverified waste; (iii) long delays between vend and waste; (iv) waste of whole doses; (v) vend and waste performed at different med stations; (vi) waste doses with another potential abuser; and (vii) vends of higher dose product that generate higher waste when exact or smaller doses are available.

12. A system for identifying potential controlled medication diverters, the system comprising:

one or more dispensing devices each configured to automatically monitor dispensing of a controlled medication and to automatically, based on receiving an authorization credential at the dispensing device, capture and associate a time and a user identify of a respective user performing a dispensing transaction at the dispensing device;

one or more processors; and a memory including instructions that, when executed by the one or more processors, cause the one or more processors to:

receive, from the one or more dispensing devices, based on respective user identities captured at the one or more dispensing devices, one or more signals associated with each medication that was dispensed from the one or more dispensing devices and the respective users who dispensed the medication from the one or more dispensing devices;

identify a plurality of user activities performed by a plurality of users in connection at least one medication and a plurality of devices, the plurality of devices including the one or more dispensing devices;

determine first factor scores for the plurality of users based on the plurality of user activities, wherein the first factor scores comprise a score for waste activities and a usage score associated with an amount of medication usage;

generate respective first diversion scores for the plurality of users based on an evaluation of the identified plurality of user activities and the first factor scores across caregivers associated with a patient population;

identify, from the plurality of users, a plurality of suspected diverters based on the generated first diversion scores for the plurality of users;

after generating the respective diversion scores and identifying the plurality of suspected diverters based on the respective diversion scores, for each identified diverter of the plurality of suspected diverters:

automatically determining one or more second factor scores for the identified diverter based on patient records for patients being cared for by the identified diverter or based on caregiver scheduling data associated with the identified diverter;

generate and store respective total diversion scores for the plurality of suspected diverters based on the first diversion scores for the suspected diverters and the second factor scores determined after identifying the plurality of suspected diverters; and automatically select, based on the respective total diversion scores and the second factor scores a plurality of selected diverter suspects from the suspected diverters; and generate a user interface that identifies the selected diverter suspects, together with, for each selected diverter suspect, a series of graphic indicators representative of the respective activities contributing to the total diversion score associated with the selected diverter suspect, wherein the user interface is configured to, when a user selects a respective graphical indicator of the series of graphic indicators, display dispensing transactions performed at one or more of the plurality of dispensing devices by the selected diverter suspect associated with the respective graphical indicator.

13. The system of claim 12, wherein a user activity of the plurality of user activities comprises a device usage associated with a single user across a plurality of distributed dispensing devices; and
   wherein determining a first diversion score for the single user comprises comparing the device usage with device usages of other users associated with the patient population.

14. The system of claim 12,
   wherein at least one factor score of the first factor scores comprises a waste score based on the user being associated with one or more of: (i) more waste than normal; (ii) unverified waste; (iii) long delays between vend and waste; (iv) waste of whole doses; (v) vend and waste performed at different med stations; (vi) waste doses with another potential abuser; and (vii) vends of higher dose product that generate higher waste when exact or smaller doses are available.

15. The system of claim 12, wherein a user activity of the plurality of user activities comprises a first user of the plurality of users dispensing a dosage of a respective medication from a dispensing device; and
   wherein determining a first diversion score of the first user comprises determining that the dosage dispensed from the dispensing device by the first user is a higher dosed product than a dosage dispensed by other users for the same patient.

16. The system of claim 12,
   wherein at least one factor score of the first factor scores comprises a score based on the user being associated with one or more of: (i) gross vends that are in a higher amount than other users in a same role as the user; (ii) vends for a care area that are in a higher amount than other users in the care area; (iii) vends of a specific drug for a care area that are in a higher amount than other users in the care area; (iv) escalating usage over a reporting period for a care area; (vi) a vend for a discharged patient; (vii) a vend at an ADC that does not normally serve a patient associated with the vend; (viii) no administration for a vend; (ix) doses higher than vended by other caregivers by frequency; (x) withdrawal from multiple automatic dispensing cabinets (ADCs) for same patient; (xi) premature vend; (xii) vend of oral medication for a nothing by mouth (NPO) patient; (xiii) vend of more doses than provided in an order; (xiv) a vend of pain medication for a patient without a pain assessment; and (xv) a vend when the user is not on duty.

* * * * *